United States Patent
Majeti et al.

(10) Patent No.: US 11,708,575 B2
(45) Date of Patent: Jul. 25, 2023

(54) RNA INTERFERENCE DELIVERY FORMULATION AND METHODS FOR MALIGNANT TUMORS

(71) Applicant: Nitto Denko Corporation, Osaka (JP)

(72) Inventors: Bharat Majeti, San Diego, CA (US); Jean-Pierre Clamme, San Diego, CA (US); Li Wang, San Diego, CA (US); Roger C. Adami, Carlsbad, CA (US); Wenbin Ying, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/685,283

(22) Filed: Nov. 15, 2019

(65) Prior Publication Data

US 2020/0157540 A1 May 21, 2020

Related U.S. Application Data

(60) Provisional application No. 62/768,826, filed on Nov. 16, 2018.

(51) Int. Cl.
| | |
|---|---|
| *A61K 47/00* | (2006.01) |
| *A61K 48/00* | (2006.01) |
| *C12N 15/113* | (2010.01) |
| *A61P 35/00* | (2006.01) |
| *A61K 31/712* | (2006.01) |
| *A61K 31/7125* | (2006.01) |
| *A61K 9/16* | (2006.01) |
| *A61K 47/24* | (2006.01) |
| *A61K 9/14* | (2006.01) |
| *A61K 9/19* | (2006.01) |
| *A61K 47/28* | (2006.01) |

(52) U.S. Cl.
CPC ............ *C12N 15/113* (2013.01); *A61K 9/141* (2013.01); *A61K 9/1652* (2013.01); *A61K 9/19* (2013.01); *A61K 31/712* (2013.01); *A61K 31/7125* (2013.01); *A61K 47/24* (2013.01); *A61K 47/28* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,173,170 B2 | 5/2012 | Niitsu et al. | |
| 9,771,582 B2 | 9/2017 | Niitsu et al. | |
| 2005/0244858 A1 | 11/2005 | Rossi et al. | |
| 2014/0315975 A1 | 10/2014 | Niitsu et al. | |
| 2016/0186182 A1* | 6/2016 | Niitsu ................... | C07F 9/6533 424/450 |
| 2016/0376229 A1 | 12/2016 | Adami et al. | |
| 2018/0235995 A1 | 8/2018 | Ying et al. | |

FOREIGN PATENT DOCUMENTS

| | | |
|---|---|---|
| JP | 2018-512373 A | 5/2018 |
| JP | 2018-524330 A | 8/2018 |
| WO | WO 1995/08563 A1 | 3/1995 |
| WO | WO 1996/40205 A1 | 12/1996 |
| WO | WO 1999/032619 A1 | 7/1999 |
| WO | WO 1999/54346 A1 | 10/1999 |
| WO | WO 2000/01846 A1 | 1/2000 |
| WO | WO 2000/044895 A1 | 8/2000 |
| WO | WO 2001/029058 A1 | 4/2001 |
| WO | WO 2001/036646 A1 | 5/2001 |
| WO | WO 2016/134146 A2 | 8/2016 |
| WO | WO 2016/134146 A3 | 8/2016 |
| WO | WO 2016/210190 A1 | 12/2016 |
| WO | WO 2017/015552 A1 | 1/2017 |

OTHER PUBLICATIONS

Deol, Biochim. Biophys. Acta. 1997, 1334: 161-172.*
Kao, BBA, 1981, 677: 453-461; Abstract.*
Ilium, J. Pharm. Sci., 1986, 75: 16-22.*
Kao et al., BBA, 1981, 677: 453-461; Abstract.*
Xiao et al., Biomaterials, 2013, 34: 9648-9656.*
Alayoubi, The AAPS Journal, 2013, 15: 1168-1179.*
Gajbhiye, Eur. J. Med. Chem., 2009, 44: 1155-1166.*
Jiang, J. Drug Targeting, 2010, 18: 389-403.*
Search Report and Written Opinion issued in International patent application No. PCT/US2019/061702, dated Feb. 6, 2020.
Aliya et al., Mol Cell Biochem., Nov. 2003; 253(1-2):319-327.
Ban et al., "Transfection of Glutathione S-Transferase (GST) Antisense Complementary DNA Increases the Sensitivity of a Colon Cancer Cell Line to Adriamycin, Cisplatin, Melphalan, and Etoposide", Cancer Res., 1996, 56(15):3577-82.
Bora, et al. "Molecular Cloning, Sequencing, and Expression of Human Myocardial Fatty Acid Ethyl Ester Synthase-III cDNA", vol. 266, No. 25, Issue of Sep. 5, p. 16774-16777, 1991.
Brody et al., "Aptamers as therapeutic and diagnostic agents", J. Biotechnol., 2000, vol. 74, pp. 5-13.
Elbashir et al., Duplexes of 21±nucleotide RNAs mediate RNA interference in cultured mammalian cells:, Nature, 2001, vol. 411, pp. 494-498.
Elbashir et al., "RNA interference is mediated by 21-and 22-nucleotide RNAs", Genes & Development, 2001, vol. 15, pp. 188-200.
Fire et al., "Potent and specific genetic interference by double-stranded RNA in Caenorhabditis elegans", Nature, 1998, vol. 391, pp. 806811.

(Continued)

*Primary Examiner* — Ileana Popa
(74) *Attorney, Agent, or Firm* — Knobbe, Martens, Olson & Bear, LLP

(57) ABSTRACT

This invention provides formulations for use in distributing RNAi molecules targeted to a human GST-π for treating a malignant tumor in a subject. The formulation can include nanoparticles composed of an ionizable lipid, a DSPE lipid, and additional lipids. A drug product can be made by lyophilization of the formulation. This invention further provides methods for ameliorating or treating a malignant tumor by administering a therapeutically effective amount of a formulation containing the RNAi agents.

17 Claims, 8 Drawing Sheets

Specification includes a Sequence Listing.

(56) References Cited

OTHER PUBLICATIONS

Gold et al., Annu Rev Biochem, 1995, vol. 64, pp. 763-797.
Hall et al., Cancer Res. 1989; 49 (22): 6265-8.
Hammond et al., "An RNA-directed nuclease mediates post-transcriptional gene silencing in *Drosophila* cells", Nature, 2000, vol. 404, pp. 293-296.
Hermann et al., "Adaptive Recognition by Nucleic Acid Aptamers", Science, 2000, vol. 287, pp. 820-825.
Hirata S. et al., Cancer, Nov. 15, 1992:70(10):2381-7.
Hokaiwado et al., "Glutathione S-transferase Pi mediates proliferation of androgen-independent prostate cancer cells", Carcinogenesis, 2008, 29(6):1134-1138.
Nakajima et al., "Reversal of Multiple Drug Resistance in Cholangiocarcinoma by the Glutathione S-Transferase-π-Specific Inhibitor O1-Hexadecyl-y-glutamyl-S-benzylcysteinyl-D-phenylglycine Ethylester", J Pharmacol Exp Ther., 2003, 306(3):861-9.
Niitsu et al., "Serum glutathione-S-transferase-pi as a tumor marker for gastrointestinal malignancies", Cancer, Jan. 15, 1989; 63(2):317-23.
Remington's Pharmaceutical Sciences, 18th Ed., Mack Publishing Co., Easton, Penn. (1990) (TOC).
Sharp, "RNAi and double-strand RNA", Genes & Development, 1999, vol. 13, pp. 139-141.
Tew et al., "Ethacrynic acid and piriprost as enhancers of cytotoxicity in drug resistant and sensitive cell lines", Cancer Res. 1988; 48 (13): 3622-5).
Zamore et al., "RNAi: Double-Stranded RNA Directs the ATP-Dependent Cleavage of mRNA at 21 to 23 Nucleotide Intervals", Cell, 2000, vol. 101, pp. 25-33.
Pandey, R., and Khuller, G.K., "Nanotechnology based drug delivery system(s) for the management of tuberculosis", Indian Journal of Experimental Biology, vol. 44, May 2006, pp. 357-366.
Vyas, S.P., et al., "Design of liposomal aerosols for improved delivery of rifampicin to alveolar macrophages", International Journal of Pharmaceutics 269 (2004) 37-49.
Richardson, S. C. W., et al., "Potential of low molecular mass chitosan as a DNA delivery system: biocompatibility, body distribution and ability to complex and protect DNA", Int. J. Pharm. 178 (1999) 231-243.
Extended European Search Report issued in EP Application No. 19884629.7, dated Jul. 7, 2022.
Office Action issued in Japanese Patent Application No. 2021-526778, dated Aug. 2, 2022.
Decision of Refusal dated Feb. 7, 2023 in Japanese Application No. 2021-526778, filed Nov. 15, 2019.
Office Action dated May 17, 2023 issued in Taiwanese Application No. 108141647, filed on Nov. 15, 2019.

\* cited by examiner

SEQUENCE LISTING

```
<160> NUMBER OF SEQ ID NOS: 52

<210> SEQ ID NO 1
<211> LENGTH: 21
<212> TYPE: DNA
<213> ORGANISM: Artificial Sequence
<220> FEATURE:
<221> NAME/KEY: modified_base
<222> LOCATION: (1)...(19)
<223> OTHER INFORMATION: ribonucleotide
<220> FEATURE:
<221> NAME/KEY: modified_base
<222> LOCATION: (20)...(21)
<223> OTHER INFORMATION: n = ribo-A, ribo-C, ribo-G, ribo-U, 2'-Ome-
      substituted ribo-U, 2'-deoxy-A, 2'-deoxy-U, 2'-deoxy-G, 2'-deoxy-
      C, deoxythymidine or modified, inverted or chemically modified
      residue
<220> FEATURE:
<223> OTHER INFORMATION: Homo sapiens

<400> SEQUENCE: 1
gaagccuuuu gagacccuan n                                             21

<210> SEQ ID NO 2
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 2
gaagccuuuu gagacccuau u                                             21

<210> SEQ ID NO 3
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 3
gaagccuuuu gagacccuau u                                             21

<210> SEQ ID NO 4
<211> LENGTH: 21
<212> TYPE: RNA
<213> ORGANISM: Artificial Sequence
<220> FEATURE:
<221> NAME/KEY: modified_base
```

```
<222> LOCATION: (20)...(21)
<223> OTHER INFORMATION: 2'-OMe-substituted
<220> FEATURE:
<223> OTHER INFORMATION: Homo sapiens

<400> SEQUENCE: 4
gaagccuuuu gagacccuau u                                              21

<210> SEQ ID NO 5
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 5
gaagccuuuu gagacccuau u                                              21

<210> SEQ ID NO 6
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 6
gaagccuuuu gagacccuau u                                              21

<210> SEQ ID NO 7
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 7
gaagccuuuu gagacccuau u                                              21

<210> SEQ ID NO 8
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 8
gaagccuuuu gagacccuau u                                              21

<210> SEQ ID NO 9
<211> LENGTH: 21
<212> TYPE: RNA
<213> ORGANISM: Artificial Sequence
<220> FEATURE:
```

-continued

<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 9
gaagccuuuu gagacccuau u                                              21

<210> SEQ ID NO 10
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 10
gaagccuuuu gagacccuau u                                              21

<210> SEQ ID NO 11
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 11
gaagccuuuu gagacccuau u                                              21

<210> SEQ ID NO 12
<211> LENGTH: 21
<212> TYPE: DNA
<213> ORGANISM: Artificial Sequence
<220> FEATURE:
<221> NAME/KEY: modified_base
<222> LOCATION: (1)...(19)
<223> OTHER INFORMATION: ribonucleotide
<220> FEATURE:
<221> NAME/KEY: modified_base
<222> LOCATION: (20)...(21)
<223> OTHER INFORMATION: deoxythymidine
<220> FEATURE:
<223> OTHER INFORMATION: Homo sapiens

<400> SEQUENCE: 12
gaagccuuuu gagacccuat t                                              21

<210> SEQ ID NO 13
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 13
gaagccuuuu gagacccuau u                                              21

```
<210> SEQ ID NO 14
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 14
gaagccuuuu gagacccuau u                                              21

<210> SEQ ID NO 15
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 15
gaagccuuuu gagacccuau u                                              21

<210> SEQ ID NO 16
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 16
gaagccuuuu gagacccuau u                                              21

<210> SEQ ID NO 17
<211> LENGTH: 21
<212> TYPE: DNA
<213> ORGANISM: Artificial Sequence
<220> FEATURE:
<221> NAME/KEY: modified_base
<222> LOCATION: (1)...(18)
<223> OTHER INFORMATION: ribonucleotide
<220> FEATURE:
<221> NAME/KEY: modified_base
<222> LOCATION: (19)...(19)
<223> OTHER INFORMATION: 2'-deoxy-2'-fluoro substitution
<220> FEATURE:
<221> NAME/KEY: modified_base
<222> LOCATION: (20)...(21)
<223> OTHER INFORMATION: 2'-OMe-subsituted ribonucleotide
<220> FEATURE:
<223> OTHER INFORMATION: Homo sapiens

<400> SEQUENCE: 17
gaagccuuuu gagacccuau u                                              21

<210> SEQ ID NO 18
<211> LENGTH: 21
<212> TYPE: DNA
<213> ORGANISM: Artificial Sequence
<220> FEATURE:
<221> NAME/KEY: modified_base
<222> LOCATION: (1)...(13)
```

```
<223> OTHER INFORMATION: ribonucleotide
<220> FEATURE:
<221> NAME/KEY: modified_base
<222> LOCATION: (14)...(14)
<223> OTHER INFORMATION: 2'-deoxy-2'-fluoro substitution
<220> FEATURE:
<221> NAME/KEY: modified_base
<222> LOCATION: (15)...(18)
<223> OTHER INFORMATION: ribonucleotide
<220> FEATURE:
<221> NAME/KEY: modified_base
<222> LOCATION: (19)...(19)
<223> OTHER INFORMATION: 2'-deoxy-2'-fluoro substitution
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 18
gaagccuuuu gagacccuau u                                              21

<210> SEQ ID NO 19
<211> LENGTH: 21
<212> TYPE: RNA
<213> ORGANISM: Artificial Sequence
<220> FEATURE:
<221> NAME/KEY: modified_base
<222> LOCATION: (19)...(21)
<223> OTHER INFORMATION: 2'-OMe-substituted
<220> FEATURE:
<223> OTHER INFORMATION: Homo sapiens

<400> SEQUENCE: 19
gaagccuuuu gagacccuau u                                              21

<210> SEQ ID NO 20
<211> LENGTH: 21
<212> TYPE: RNA
<213> ORGANISM: Artificial Sequence
<220> FEATURE:
<221> NAME/KEY: modified_base
<222> LOCATION: (19)...(21)
<223> OTHER INFORMATION: 2'-OMe-substituted
<220> FEATURE:
<223> OTHER INFORMATION: Homo sapiens

<400> SEQUENCE: 20
gaagccuuuu gagacccuau u                                              21

<210> SEQ ID NO 21
<211> LENGTH: 21
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 21
gaagccuuuu gagacccuau u                                              21

<210> SEQ ID NO 22
<211> LENGTH: 21
```

```
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (8)...(8)
<223> OTHER INFORMATION: 2'-OMe-substituted
<220> FEATURE:
<221> NAME/KEY: modified_base
<222> LOCATION: (10)...(10)
<223> OTHER INFORMATION: 2'-OMe-substituted
<220> FEATURE:
<221> NAME/KEY: modified_base
<222> LOCATION: (18)...(18)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 22
gaagccuuuu gagacccuau u                                              21

<210> SEQ ID NO 23
<211> LENGTH: 21
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 23
gaagccuuuu gagacccuau u                                              21

<210> SEQ ID NO 24
<211> LENGTH: 21
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (8)...(8)
<223> OTHER INFORMATION: 2'-OMe-substituted
<220> FEATURE:
<221> NAME/KEY: modified_base
<222> LOCATION: (10)...(10)
<223> OTHER INFORMATION: 2'-OMe-substituted
<220> FEATURE:
<221> NAME/KEY: modified_base
<222> LOCATION: (18)...(18)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 24
```
gaagccuuuu gagacccuau u                                                      21

<210> SEQ ID NO 25
<211> LENGTH: 21
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (8)...(8)
<223> OTHER INFORMATION: 2'-OMe-substituted
<220> FEATURE:
<221> NAME/KEY: modified_base
<222> LOCATION: (10)...(10)
<223> OTHER INFORMATION: 2'-OMe-substituted
<220> FEATURE:
<221> NAME/KEY: modified_base
<222> LOCATION: (18)...(21)
<223> OTHER INFORMATION: 2'-OMe-substituted
<220> FEATURE:
<223> OTHER INFORMATION: Homo sapiens

<400> SEQUENCE: 25
gaagccuuuu gagacccuau u                                                      21

<210> SEQ ID NO 26
<211> LENGTH: 21
<212> TYPE: RNA
<213> ORGANISM: Artificial Sequence
<220> FEATURE:
<221> NAME/KEY: modified_base
<222> LOCATION: (1)...(3)
<223> OTHER INFORMATION: 2'-OMe-substituted
<220> FEATURE:
<221> NAME/KEY: modified_base
<222> LOCATION: (8)...(8)
<223> OTHER INFORMATION: 2'-OMe-substituted
<220> FEATURE:
<221> NAME/KEY: modified_base
<222> LOCATION: (10)...(10)
<223> OTHER INFORMATION: 2'-OMe-substituted
<220> FEATURE:
<221> NAME/KEY: modified_base
<222> LOCATION: (18)...(21)
<223> OTHER INFORMATION: 2'-OMe-substituted
<220> FEATURE:
<223> OTHER INFORMATION: Homo sapiens

<400> SEQUENCE: 26
gaagccuuuu gagacccuau u                                                      21

<210> SEQ ID NO 27
<211> LENGTH: 21
<212> TYPE: DNA
<213> ORGANISM: Artificial Sequence
<220> FEATURE:
<221> NAME/KEY: modified_base
<222> LOCATION: (1)...(19)
<223> OTHER INFORMATION: ribonucleotide
<220> FEATURE:
<221> NAME/KEY: modified_base
<222> LOCATION: (20)...(21)
<223> OTHER INFORMATION: n = ribo-A, ribo-C, ribo-G, ribo-U, 2'-Ome-
      substituted ribo-U, 2'-deoxy-A, 2'-deoxy-U, 2'-deoxy-G, 2'-deoxy-
      C, deoxythymidine or modified, inverted or chemically modified
      residue
<220> FEATURE:
<223> OTHER INFORMATION: Homo sapiens

<400> SEQUENCE: 27
uagggucuca aaaggcuucn n                                                21

<210> SEQ ID NO 28
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 28
uagggucuca aaaggcuucu u                                                21

<210> SEQ ID NO 29
<211> LENGTH: 21
<212> TYPE: DNA
<213> ORGANISM: Artificial Sequence
<220> FEATURE:
<221> NAME/KEY: modified_base
<222> LOCATION: (1)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 29
uagggucuca aaaggcuucu u                                                21

<210> SEQ ID NO 30
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: ribonucleotide
<220> FEATURE:
<221> NAME/KEY: modified_base
<222> LOCATION: (2)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 30
uagggucuca aaaggcuucu u                                                21

<210> SEQ ID NO 31
<211> LENGTH: 21
<212> TYPE: DNA
<213> ORGANISM: Artificial Sequence
<220> FEATURE:
<221> NAME/KEY: modified_base
<222> LOCATION: (1)...(2)
<223> OTHER INFORMATION: ribonucleotide

```
<220> FEATURE:
<221> NAME/KEY: modified_base
<222> LOCATION: (3)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 31
uagggucuca aaaggcuucu u                                              21

<210> SEQ ID NO 32
<211> LENGTH: 21
<212> TYPE: DNA
<213> ORGANISM: Artificial Sequence
<220> FEATURE:
<221> NAME/KEY: modified_base
<222> LOCATION: (1)...(3)
<223> OTHER INFORMATION: ribonucleotide
<220> FEATURE:
<221> NAME/KEY: modified_base
<222> LOCATION: (4)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 32
uagggucuca aaaggcuucu u                                              21

<210> SEQ ID NO 33
<211> LENGTH: 21
<212> TYPE: DNA
<213> ORGANISM: Artificial Sequence
<220> FEATURE:
<221> NAME/KEY: modified_base
<222> LOCATION: (1)...(4)
<223> OTHER INFORMATION: ribonucleotide
<220> FEATURE:
<221> NAME/KEY: modified_base
<222> LOCATION: (5)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 33
uagggucuca aaaggcuucu u                                              21

<210> SEQ ID NO 34
<211> LENGTH: 21
<212> TYPE: DNA
```

```
<213> ORGANISM: Artificial Sequence
<220> FEATURE:
<221> NAME/KEY: modified_base
<222> LOCATION: (1)...(1)
<223> OTHER INFORMATION: 2'-deoxy
<220> FEATURE:
<221> NAME/KEY: modified_base
<222> LOCATION: (2)...(2)
<223> OTHER INFORMATION: ribonucleotide
<220> FEATURE:
<221> NAME/KEY: modified_base
<222> LOCATION: (3)...(3)
<223> OTHER INFORMATION: 2'-deoxy
<220> FEATURE:
<221> NAME/KEY: modified_base
<222> LOCATION: (4)...(4)
<223> OTHER INFORMATION: ribonucleotide
<220> FEATURE:
<221> NAME/KEY: modified_base
<222> LOCATION: (5)...(5)
<223> OTHER INFORMATION: 2'-deoxy
<220> FEATURE:
<221> NAME/KEY: modified_base
<222> LOCATION: (6)...(6)
<223> OTHER INFORMATION: ribonucleotide
<220> FEATURE:
<221> NAME/KEY: modified_base
<222> LOCATION: (7)...(7)
<223> OTHER INFORMATION: 2'-deoxy
<220> FEATURE:
<221> NAME/KEY: modified_base
<222> LOCATION: (8)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 34
uagggucuca aaaggcuucu u                                              21

<210> SEQ ID NO 35
<211> LENGTH: 21
<212> TYPE: DNA
<213> ORGANISM: Artificial Sequence
<220> FEATURE:
<221> NAME/KEY: modified_base
<222> LOCATION: (1)...(2)
<223> OTHER INFORMATION: ribonucleotide
<220> FEATURE:
<221> NAME/KEY: modified_base
<222> LOCATION: (3)...(3)
<223> OTHER INFORMATION: 2'-deoxy
<220> FEATURE:
<221> NAME/KEY: modified_base
<222> LOCATION: (4)...(4)
<223> OTHER INFORMATION: ribonucleotide
<220> FEATURE:
<221> NAME/KEY: modified_base
<222> LOCATION: (5)...(5)
<223> OTHER INFORMATION: 2'-deoxy
<220> FEATURE:
<221> NAME/KEY: modified_base
<222> LOCATION: (6)...(6)
<223> OTHER INFORMATION: ribonucleotide
<220> FEATURE:
<221> NAME/KEY: modified_base
<222> LOCATION: (7)...(7)
<223> OTHER INFORMATION: 2'-deoxy
<220> FEATURE:
<221> NAME/KEY: modified_base
<222> LOCATION: (8)...(19)
<223> OTHER INFORMATION: ribonucleotide
<220> FEATURE:
<221> NAME/KEY: modified_base
```

-continued

<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 35
uagggucuca aaaggcuucu u                                              21

<210> SEQ ID NO 36
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: ribonucleotide
<220> FEATURE:
<221> NAME/KEY: modified_base
<222> LOCATION: (2)...(2)
<223> OTHER INFORMATION: 2'-deoxy
<220> FEATURE:
<221> NAME/KEY: modified_base
<222> LOCATION: (3)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 36
uagggucuca aaaggcuucu u                                              21

<210> SEQ ID NO 37
<211> LENGTH: 21
<212> TYPE: DNA
<213> ORGANISM: Artificial Sequence
<220> FEATURE:
<221> NAME/KEY: modified_base
<222> LOCATION: (1)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:

```
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 37
uagggucuca aaaggcuucu u                                              21

<210> SEQ ID NO 38
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: ribonucleotide
<220> FEATURE:
<221> NAME/KEY: modified_base
<222> LOCATION: (2)...(8)
<223> OTHER INFORMATION: 2'-deoxy
<220> FEATURE:
<221> NAME/KEY: modified_base
<222> LOCATION: (9)...(13)
<223> OTHER INFORMATION: ribonucleotide
<220> FEATURE:
<221> NAME/KEY: modified_base
<222> LOCATION: (14)...(14)
<223> OTHER INFORMATION: 2'-OMe-substituted ribonucleotide
<220> FEATURE:
<221> NAME/KEY: modified_base
<222> LOCATION: (15)...(15)
<223> OTHER INFORMATION: ribonucleotide
<220> FEATURE:
<221> NAME/KEY: modified_base
<222> LOCATION: (16)...(16)
<223> OTHER INFORMATION: 2'-OMe-substituted ribonucleotide
<220> FEATURE:
<221> NAME/KEY: modified_base
<222> LOCATION: (17)...(17)
<223> OTHER INFORMATION: ribonucleotide
<220> FEATURE:
<221> NAME/KEY: modified_base
<222> LOCATION: (18)...(18)
<223> OTHER INFORMATION: 2'-OMe-substituted ribonucleotide
<220> FEATURE:
<221> NAME/KEY: modified_base
<222> LOCATION: (19)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 38
uagggucuca aaaggcuucu u                                              21
```

```
<210> SEQ ID NO 39
<211> LENGTH: 21
<212> TYPE: RNA
<213> ORGANISM: Artificial Sequence
<220> FEATURE:
<221> NAME/KEY: modified_base
<222> LOCATION: (1)...(1)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 39
uagggucuca aaaggcuucu u                                              21

<210> SEQ ID NO 40
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 40
uagggucuca aaaggcuucu u                                              21

<210> SEQ ID NO 41
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy
<220> FEATURE:
<221> NAME/KEY: modified_base
<222> LOCATION: (2)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 41
uagggucuca aaaggcuucu u                                              21

<210> SEQ ID NO 42
<211> LENGTH: 21
<212> TYPE: RNA
<213> ORGANISM: Artificial Sequence
<220> FEATURE:
<221> NAME/KEY: modified_base
<222> LOCATION: (2)...(2)
<223> OTHER INFORMATION: Phosphorothiate type linkage
<220> FEATURE:
<221> NAME/KEY: modified_base
<222> LOCATION: (20)...(21)
```

```
<223> OTHER INFORMATION: 2'-OMe-substituted
<220> FEATURE:
<223> OTHER INFORMATION: Homo sapiens

<400> SEQUENCE: 42
uagggucuca aaaggcuucu u                                              21

<210> SEQ ID NO 43
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(8)
<223> OTHER INFORMATION: ribonucleotide
<220> FEATURE:
<221> NAME/KEY: modified_base
<222> LOCATION: (9)...(9)
<223> OTHER INFORMATION: 2'-deoxy-2'-fluoro substitution
<220> FEATURE:
<221> NAME/KEY: modified_base
<222> LOCATION: (10)...(16)
<223> OTHER INFORMATION: ribonucleotide
<220> FEATURE:
<221> NAME/KEY: modified_base
<222> LOCATION: (17)...(17)
<223> OTHER INFORMATION: 2'-deoxy-2'-fluoro substitution
<220> FEATURE:
<221> NAME/KEY: modified_base
<222> LOCATION: (18)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 43
uagggucuca aaaggcuucu u                                              21

<210> SEQ ID NO 44
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(8)
<223> OTHER INFORMATION: ribonucleotide
<220> FEATURE:
<221> NAME/KEY: modified_base
<222> LOCATION: (9)...(9)
<223> OTHER INFORMATION: 2'-deoxy-2'-fluoro substitution
<220> FEATURE:
<221> NAME/KEY: modified_base
<222> LOCATION: (10)...(10)
<223> OTHER INFORMATION: ribonucleotide
<220> FEATURE:
<221> NAME/KEY: modified_base
<222> LOCATION: (11)...(12)
<223> OTHER INFORMATION: 2'-deoxy-2'-fluoro substitution
<220> FEATURE:
<221> NAME/KEY: modified_base
<222> LOCATION: (13)...(16)
<223> OTHER INFORMATION: ribonucleotide
<220> FEATURE:
<221> NAME/KEY: modified_base
```

```
<222> LOCATION: (17)...(17)
<223> OTHER INFORMATION: 2'-deoxy-2'-fluoro substitution
<220> FEATURE:
<221> NAME/KEY: modified_base
<222> LOCATION: (18)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 44
uagggucuca aaaggcuucu u                                              21

<210> SEQ ID NO 45
<211> LENGTH: 21
<212> TYPE: RNA
<213> ORGANISM: Artificial Sequence
<220> FEATURE:
<221> NAME/KEY: modified_base
<222> LOCATION: (1)...(1)
<223> OTHER INFORMATION: 2'-OMe-substituted
<220> FEATURE:
<221> NAME/KEY: modified_base
<222> LOCATION: (9)...(9)
<223> OTHER INFORMATION: 2'-OMe-substituted
<220> FEATURE:
<221> NAME/KEY: modified_base
<222> LOCATION: (17)...(17)
<223> OTHER INFORMATION: 2'-OMe-substituted
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 45
uagggucuca aaaggcuucu u                                              21

<210> SEQ ID NO 46
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(8)
<223> OTHER INFORMATION: ribonucleotide
<220> FEATURE:
<221> NAME/KEY: modified_base
<222> LOCATION: (9)...(9)
<223> OTHER INFORMATION: 2'-OMe-substituted ribonucleotide
<220> FEATURE:
<221> NAME/KEY: modified_base
<222> LOCATION: (10)...(16)
<223> OTHER INFORMATION: ribonucleotide
<220> FEATURE:
<221> NAME/KEY: modified_base
<222> LOCATION: (17)...(17)
<223> OTHER INFORMATION: 2'-OMe-substituted ribonucleotide
<220> FEATURE:
<221> NAME/KEY: modified_base
<222> LOCATION: (18)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
```

```
<223> OTHER INFORMATION: Homo sapiens

<400> SEQUENCE: 46
uagggucuca aaaggcuucu u                                              21

<210> SEQ ID NO 47
<211> LENGTH: 21
<212> TYPE: RNA
<213> ORGANISM: Artificial Sequence
<220> FEATURE:
<221> NAME/KEY: modified_base
<222> LOCATION: (20)...(21)
<223> OTHER INFORMATION: 2'-OMe-substituted
<220> FEATURE:
<223> OTHER INFORMATION: Homo sapiens

<400> SEQUENCE: 47
uagggucuca aaaggcuucu u                                              21

<210> SEQ ID NO 48
<211> LENGTH: 21
<212> TYPE: DNA
<213> ORGANISM: Artificial Sequence
<220> FEATURE:
<221> NAME/KEY: modified_base
<222> LOCATION: (1)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 48
uagggucuca aaaggcuucu u                                              21

<210> SEQ ID NO 49
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(3)
<223> OTHER INFORMATION: ribonucleotide
```

-continued

```
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(9)
<223> OTHER INFORMATION: 2'-OMe-substituted ribonucleotide
<220> FEATURE:
<221> NAME/KEY: modified_base
<222> LOCATION: (10)...(10)
<223> OTHER INFORMATION: ribonucleotide
<220> FEATURE:
<221> NAME/KEY: modified_base
<222> LOCATION: (11)...(12)
<223> OTHER INFORMATION: 2'-OMe-substituted ribonucleotide
<220> FEATURE:
<221> NAME/KEY: modified_base
<222> LOCATION: (13)...(17)
<223> OTHER INFORMATION: ribonucleotide
<220> FEATURE:
<221> NAME/KEY: modified_base
<222> LOCATION: (18)...(18)
<223> OTHER INFORMATION: 2'-OMe-substituted ribonucleotide
<220> FEATURE:
<221> NAME/KEY: modified_base
<222> LOCATION: (19)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 49
uagggucuca aaaggcuucu u                                            21

<210> SEQ ID NO 50
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
```

-continued

```
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(9)
<223> OTHER INFORMATION: 2'-OMe-substituted ribonucleotide
<220> FEATURE:
<221> NAME/KEY: modified_base
<222> LOCATION: (10)...(10)
<223> OTHER INFORMATION: ribonucleotide
<220> FEATURE:
<221> NAME/KEY: modified_base
<222> LOCATION: (11)...(12)
<223> OTHER INFORMATION: 2'-OMe-substituted ribonucleotide
<220> FEATURE:
<221> NAME/KEY: modified_base
<222> LOCATION: (13)...(17)
<223> OTHER INFORMATION: ribonucleotide
<220> FEATURE:
<221> NAME/KEY: modified_base
<222> LOCATION: (18)...(18)
<223> OTHER INFORMATION: 2'-OMe-substituted ribonucleotide
<220> FEATURE:
<221> NAME/KEY: modified_base
<222> LOCATION: (19)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 50
uagggucuca aaaggcuucu u                                            21

<210> SEQ ID NO 51
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
```

```
<222> LOCATION: (9)...(9)
<223> OTHER INFORMATION: 2'-OMe-substituted ribonucleotide
<220> FEATURE:
<221> NAME/KEY: modified_base
<222> LOCATION: (10)...(10)
<223> OTHER INFORMATION: ribonucleotide
<220> FEATURE:
<221> NAME/KEY: modified_base
<222> LOCATION: (11)...(12)
<223> OTHER INFORMATION: 2'-OMe-substituted ribonucleotide
<220> FEATURE:
<221> NAME/KEY: modified_base
<222> LOCATION: (13)...(16)
<223> OTHER INFORMATION: ribonucleotide
<220> FEATURE:
<221> NAME/KEY: modified_base
<222> LOCATION: (17)...(18)
<223> OTHER INFORMATION: 2'-OMe-substituted ribonucleotide
<220> FEATURE:
<221> NAME/KEY: modified_base
<222> LOCATION: (19)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 51
uagggucuca aaaggcuucu u                                              21

<210> SEQ ID NO 52
<211> LENGTH: 21
<212> TYPE: DNA
<213> ORGANISM: Artificial Sequence
<220> FEATURE:
<221> NAME/KEY: modified_base
<222> LOCATION: (1)...(1)
<223> OTHER INFORMATION: 2'-deoxy-2'-fluoro substitution
<220> FEATURE:
<221> NAME/KEY: modified_base
<222> LOCATION: (2)...(3)
<223> OTHER INFORMATION: ribonucleotide
<220> FEATURE:
<221> NAME/KEY: modified_base
<222> LOCATION: (4)...(4)
<223> OTHER INFORMATION: 2'-deoxy
<220> FEATURE:
<221> NAME/KEY: modified_base
<222> LOCATION: (5)...(5)
<223> OTHER INFORMATION: ribonucleotide
<220> FEATURE:
<221> NAME/KEY: modified_base
<222> LOCATION: (6)...(6)
<223> OTHER INFORMATION: 2'-deoxy
<220> FEATURE:
<221> NAME/KEY: modified_base
<222> LOCATION: (7)...(7)
<223> OTHER INFORMATION: ribonucleotide
<220> FEATURE:
<221> NAME/KEY: modified_base
<222> LOCATION: (8)...(8)
<223> OTHER INFORMATION: 2'-deoxy
<220> FEATURE:
<221> NAME/KEY: modified_base
<222> LOCATION: (9)...(9)
<223> OTHER INFORMATION: 2'-OMe-substituted ribonucleotide
<220> FEATURE:
<221> NAME/KEY: modified_base
<222> LOCATION: (10)...(10)
<223> OTHER INFORMATION: ribonucleotide
<220> FEATURE:
<221> NAME/KEY: modified_base
<222> LOCATION: (11)...(12)
<223> OTHER INFORMATION: 2'-OMe-substituted ribonucleotide
<220> FEATURE:
```

```
<221> NAME/KEY: modified_base
<222> LOCATION: (13)...(16)
<223> OTHER INFORMATION: ribonucleotide
<220> FEATURE:
<221> NAME/KEY: modified_base
<222> LOCATION: (17)...(18)
<223> OTHER INFORMATION: 2'-OMe-substituted ribonucleotide
<220> FEATURE:
<221> NAME/KEY: modified_base
<222> LOCATION: (19)...(19)
<223> OTHER INFORMATION: ribonucleotide
<220> FEATURE:
<221> NAME/KEY: modified_base
<222> LOCATION: (20)...(21)
<223> OTHER INFORMATION: 2'-OMe-substituted ribonucleotide
<220> FEATURE:
<223> OTHER INFORMATION: Homo sapiens

<400> SEQUENCE: 52
uagggucuca aaaggcuucu u                                              21
```

RNA INTERFERENCE DELIVERY FORMULATION AND METHODS FOR MALIGNANT TUMORS

REFERENCE TO RELATED APPLICATIONS

This application claims priority to U.S. Ser. No. 62/768,826, filed Nov. 16, 2018, which is hereby incorporated herein by reference in its entirety.

SEQUENCE LISTING

This application includes a Sequence Listing submitted electronically as a file named HRAK001.014.txt and having a size of approximately 26 KB, which is hereby incorporated by reference in its entirety.

TECHNICAL FIELD

This invention relates to the fields of biopharmaceuticals and therapeutics composed of nucleic acid based molecules. More particularly, this invention relates to methods and compositions for delivering RNA interference agents for preventing, treating or ameliorating the effects of conditions and diseases involving malignant tumors.

BACKGROUND

Mutation of a KRAS gene can be related to malignant tumors, such as lung adenocarcinoma, mucinous adenoma, and colorectal carcinoma. Recent observations indicate that elevated levels of the protein Glutathione S-transferase-$\pi$ (GST-$\pi$) is associated with such KRAS mutations.

GST-$\pi$ is a member of the Glutathione S-transferase (IUBMB EC 2.5.1.18) family of six isoenzymes that play a role in detoxification by catalyzing the conjugation of hydrophobic and electrophilic compounds with reduced glutathione. The GST-$\pi$ gene (GSTP1) is a polymorphic gene encoding active, functionally different GSTP1 variant proteins that are thought to function in xenobiotic metabolism. GSTP1 may play a role in susceptibility to cancer and is expressed abundantly in tumor cells. See, e.g., Aliya S. et al. Mol Cell Biochem., 2003 November; 253(1-2):319-327. Glutathione S-transferase-$\pi$ is an enzyme that in humans is encoded by the GSTP1 gene. See, e.g., Bora P S, et al. (October 1991) J. Biol. Chem., 266 (25): 16774-16777. The GST-$\pi$ isoenzyme has been shown to catalyze the conjugation of GSH with some alkylating anti-cancer agents, suggesting that over-expression of GST-$\pi$ would result in tumor cell resistance.

Elevated serum GST-$\pi$ levels were observed in patients with various gastrointestinal malignancies including gastric, esophageal, colonic, hepatocellular, and biliary tract cancers. Over 80% of patients with Stage III or IV gastric cancer and even about 50% of those with Stage I and II had elevated levels of serum GST-$\pi$. See, e.g., Niitsu Y, et al. Cancer, 1989 Jan. 15; 63(2):317-23. GST-$\pi$ was found to be a useful marker for predicting the recurrence of tumors in patients with oral cancer after chemotherapy. See, e.g., Hirata S. et al. Cancer, 1992 Nov. 15:70(10):2381-7.

Expression of GST-$\pi$ increases in various cancer cells, which may be related to resistance to some anticancer agents. See, e.g. Ban et al., Cancer Res., 1996, 56(15):3577-82; Nakajima et al., J Pharmacol Exp Ther., 2003, 306(3): 861-9.

Agents for suppressing GST-$\pi$ have been disclosed for inducing apoptosis in cells. However, such compositions and techniques also caused autophagy and required the combined action of various agents. See, e.g., US 2014/0315975 A1. Moreover, suppressing GST-$\pi$ has not been found to shrink or reduce tumors. For example, in a cancer that was overexpressing GST-$\pi$, the weights of tumors were not affected by suppressing GST-7C, although other effects were observed. See, e.g., Hokaiwado et al., Carcinogenesis, 2008, 29(6):1134-1138.

There is an urgent need for methods and compositions to develop therapies for patients with malignancies, such as siRNA agents, compounds and structures for inhibition of expression of GST-$\pi$.

What is needed are methods and compositions for preventing or treating malignant tumors. There is a continuing need for RNAi molecules, and other structures and compositions for preventing, treating, or reducing malignant tumors.

BRIEF SUMMARY

This invention provides compositions and methods for therapeutic use of RNAi molecules that are targeted to human GST-$\pi$, in combination with a pharmaceutically acceptable carrier.

Various embodiments relate to molecules and compositions thereof for use in biopharmaceuticals and therapeutics for malignant tumors. More particularly, various embodiments relate to compounds, compositions and methods for providing nanoparticles to deliver and distribute active agents or drug compounds to cells, tissues, organs, and subjects having malignant tumors.

Included are methods for preventing, treating or ameliorating one or more symptoms of a malignant tumor in a subject in need. The method can involve administering to the subject an effective amount of a composition of RNAi molecules targeted to GST-$\pi$.

Embodiments of this invention include the following:

A pharmaceutical composition comprising (a) a nucleic acid active pharmaceutical ingredient (API); such as, for example, API(26/52), a siRNA targeted to GST-$\pi$ having the sequence

```
sense strand SEQ ID NO: 26 (5'->3'):
GAAGCCUUUUGAGACCCUAUU antisense strand SEQ ID NO: 52 (5'->3'):
fUAGgGuCuCAAAAGGCUUCUU;
``` wherein A, G, C and U refer to ribo-A, ribo-G, ribo-C and ribo-U, respectively; lower case letters a, u, g, c, t refer to 2'-deoxy-A, 2'-deoxy-U, 2'-deoxy-G, 2'-deoxy-C, and deoxythymidine (dT=T=t) respectively; underlining refers to 2'-OMe-substituted, e.g., U; the lower case letter f refers to 2'-deoxy-2'-fluoro substitution, e.g. fU is 2'-deoxy-2'-fluoro-U; hereinafter referred to as API(26/52);
and also containing (b) a compound having the following Formula II:

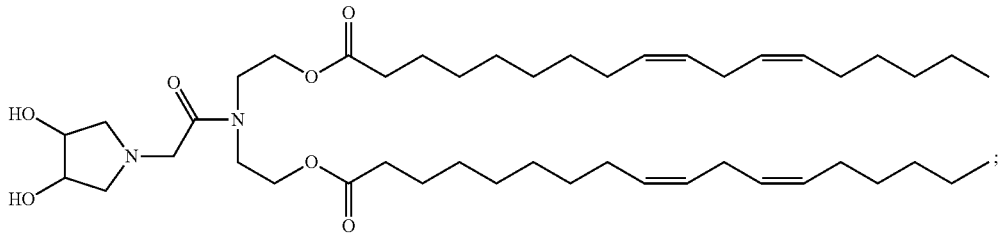 [SMILES: CCCCC/C=C\C/C=C\CCCCCCCC(=O)OCCN(CCOC(=O)CCCCCCC/C=C\C/C=C\CCCCC)C(=O)CN1CC(O)C(O)C1]

such as, for example, Compound A having the structure described elsewhere herein;

(c) a DSPE lipid; such as, for example, a DSPE lipid comprising a polyethyleneglycol (PEG) region, a multi-branched PEG region, a methoxypolyethyleneglycol (mPEG) region, a carbonyl-methoxypolyethyleneglycol region, or a polyglycerine region;

(d) a sterol lipid; and (e) one or more neutral lipids.

The compound of Formula II (e.g., Compound A) may be from 15 mol % to 35 mol % of the total lipids of the composition, or from 20 mol % to 30 mol % of the total lipids of the composition.

A sterol may be from 25 mol % to 40 mol % of the total lipids of the composition, or from 30 mol % to 40 mol % of the total lipids of the composition. The sterol can be cholesterol.

The DSPE lipid may be from, 1 mol % to 10 mol %, or 1 mol % to 8 mol %, or 4 mol % to 6 mol %, of the total lipids of the composition. The DSPE lipid may have a polyethyleneglycol (PEG) region, a multi-branched PEG region, a methoxypolyethyleneglycol (mPEG) region, a carbonyl-methoxypolyethyleneglycol region, or a polyglycerine region. In certain embodiments, the DSPE lipid is DSPE-mPEG-2000.

The sum of the one or more neutral lipids may be from 25 mol % to 45 mol % of the total lipids of the composition, wherein each of the neutral lipids individually is from 5 mol % to 40% mol %. In certain embodiments, the sum of the one or more neutral lipids can be from 30 mol % to 40 mol % of the total lipids of the composition, wherein each of the neutral lipids individually is from 10 mol % to 30% mol %. The one or more neutral lipids can be selected from phosphatidyl ethanolamine compounds and phosphatidyl choline compounds. The one or more neutral lipids may comprise or consist of 1,2-dioleoyl-sn-Glycero-3-Phosphocholine (DOPC) and 1,2-dioleoyl-sn-glycero-3-phosphoethanolamine (DOPE). The cholesterol, DOPC, and DOPE combined can be 50 mol % to 85 mol % of the total lipids of the composition.

Various embodiments relate to a pharmaceutical composition, wherein a compound of Formula II (e.g., Compound A) comprises 15 mol % to 35 mol % of the total lipids of the composition;

cholesterol, DOPC, and DOPE combined comprise 50 mol % to 85 mol % of the total lipids of the composition;

DSPE-mPEG-2000 comprises from 1 mol % to 10 mol %, or 1 mol % to 8 mol %, or 4 mol % to 6 mol %, of the total lipids of the composition; and wherein the compound of Formula II (e.g., Compound A), cholesterol, DOPC, DOPE, and DSPE-mPEG-2000 combined comprise at least 97 mol % (e.g., 100 mol %) of the total lipids of the composition.

Embodiments of this invention include a pharmaceutical composition, wherein a compound of Formula II (e.g., (e.g., Compound A) comprises 20 mol % to 30 mol % of the total lipids of the composition;

cholesterol comprises 25 mol % to 35 mol % of the total lipids of the composition; DOPC and DOPE combined comprise 30 mol % to 50 mol % of the total lipids of the composition;

DSPE-mPEG-2000 comprises from 1 mol % to 10 mol %, or 1 mol % to 8 mol %, or 4 mol % to 6 mol %, of the total lipids of the composition; and wherein the compound of Formula II (e.g., Compound A), cholesterol, DOPC, DOPE, and DSPE-mPEG-2000 combined comprise at least 97% (e.g., 100 mol %) of the total lipids of the composition.

In an embodiment, this invention includes a pharmaceutical composition, comprising
10 mg API(26/52), Compound A (24-26 mol % of total lipids), cholesterol (29-31 mol % of total lipids), DOPE (19-21 mol % of total lipids), DOPC (19-21 mol % of total lipids), and DSPE-mPEG-2000 (4-6 mol % of total lipids).

In an embodiment, this invention includes a pharmaceutical composition, comprising
10 mg API(26/52), 49.1 mg Compound A (about 25.0 mol % of total lipids), 29.5 mg semi-synthetic cholesterol (about 30.0 mol % of total lipids), 37.8 mg DOPE (about 20.0 mol % of total lipids), 40.0 mg DOPC (about 20.0 mol % of total lipids), and 35.6 mg DSPE-mPEG-2000 (about 4.99 mol % of total lipids).

In an embodiment, this invention includes a pharmaceutical composition, comprising
10 mg API(26/52), 49.1 mg Compound A (about 24.98 mol % of total lipids), 29.5 mg semi-synthetic cholesterol (about 30.01 mol % of total lipids), 37.8 mg DOPE (about 19.99 mol % of total lipids), 40.0 mg DOPC (about 20.02 mol % of total lipids), and 35.6 mg DSPE-mPEG-2000 (about 4.992 mol % of total lipids).

In an embodiment, this invention includes a pharmaceutical composition, comprising
10 mg API(26/52), 49.1 mg Compound A (24.985 mol % of total lipids), 29.5 mg semi-synthetic cholesterol (30.015 mol % of total lipids), 37.8 mg DOPE (19.989 mol % of total lipids), 40.0 mg DOPC (20.019 mol % of total lipids), and 35.6 mg DSPE-mPEG-2000 (4.992 mol % of total lipids).

A pharmaceutical composition can comprise nanoparticles encapsulating the API (e.g., API(26/52)), wherein the nanoparticles have a Z-average size of 30 to 100 nm.

A pharmaceutical composition can comprise nanoparticles encapsulating the API (e.g., API(26/52)), wherein the nanoparticles have a Z-average size of 46 nm and a PDI of 0.097.

In some embodiments, a pharmaceutical composition can comprise nanoparticles having a PDI of less than 0.30.

In some embodiments, a pharmaceutical solution can comprise solvents ethanol and water for injection, as well as sucrose, 2-hydroxypropyl-β-cyclodextrin, a buffer, and a suspension of a pharmaceutical composition above. The buffer may be selected from an acetate buffer, a citrate buffer, and a phosphate buffer. In certain embodiments, the buffer is selected from acetic acid and sodium acetate, citric acid and sodium citrate, and potassium dihydrogen phosphate and disodium hydrogen phosphate dehydrate, and may further comprise sodium chloride.

Embodiments of this invention further contemplate pharmaceutical compositions being a solid lyophile of the pharmaceutical solution above. A drug product may comprise a vial containing a lyophilized cake of the pharmaceutical solution above, wherein the headspace of the vial is filled with nitrogen gas. The lyophilized cake may contain sucrose, 2-hydroxypropyl-β-cyclodextrin, sodium acetate, and lyophilized residue of the pharmaceutical composition.

The lyophilized cake may comprise 700 mg sucrose, 467 mg 2-hydroxypropyl-3-cyclodextrin, 2.7 mg sodium acetate, and lyophilized residue of the pharmaceutical composition. The drug product vial may be a clear, 20 mL USP Type I glass vial, sealed with a barrier film stopper and a flip off aluminum seal.

Other embodiments of this invention include a kit comprising the drug product and instructions for reconstituting the lyophilized cake and administering a reconstituted formulation to a subject. The kit may comprise a sterile diluent for reconstituting the lyophilized cake, and an IV infusion bag.

In various embodiments, a drug for administration by infusion may comprise a reconstituted solution of a lyophilized cake of a drug product in a sterile diluent. As used herein, the term "diluent" refers to an ingredient in a pharmaceutical composition that lacks pharmacological activity but may be pharmaceutically necessary or desirable. For example, a diluent may be used to increase the effective bulk of a potent drug to facilitate administration, such as by dispersing or dissolving a drug in a liquid for administration by injection, ingestion or inhalation. The diluent can be a sodium acetate solution, such as Sodium Acetate Injection, USP. The drug solution may contain a concentration of the API, such as API(26/52), for example 1.5 mg/mL, and may comprise liposome nanoparticles encapsulating the API (e.g., API(26/52)).

In a drug solution embodiment, the nanoparticles can be 10 to 150 nm in size, or 45 to 65 nm in size. The PDI of the nanoparticles can be less than 0.30. The average charge of the nanoparticles can be −10 mV to +10 mV.

A drug may further comprise one or more pharmaceutically acceptable excipients, such as a pharmaceutically acceptable tonicity excipient. As used herein, an "excipient" is an inert substance that is included in a pharmaceutical composition to provide a desirable physical property such as bulk, consistency, stability, binding ability, lubrication, disintegrating ability etc., to the composition. A "diluent" is a type of excipient. In certain embodiments, the tonicity excipient can be sucrose or 2-hydroxypropyl-β-cyclodextrin.

A drug may further comprise a pharmaceutically acceptable pH adjusting excipient, for example, sodium hydroxide, where the pH of the drug may be 5 to 6.

Embodiments of this invention further contemplate methods for treating or ameliorating one or more symptoms of cancer in a subject in need thereof, the method comprising administering to the subject a therapeutically effective amount of a drug described above. The drug can be administered by parenteral infusion for 30 to 120 minutes. The cancer may be lung cancer. The administration may decrease expression of GST-π in the subject by at least 5% for at least 5 days. The administration can be by intravenous injection, subcutaneous injection, intraperitoneal injection, intravenous infusion, or intraperitoneal infusion.

Various embodiments relate to a use of a drug product in medical therapy, and for treating or ameliorating one or more symptoms of cancer, including lung cancer. A drug product may be used in the manufacture of a medicament for treating or ameliorating one or more symptoms of cancer.

BRIEF DESCRIPTION OF THE DRAWINGS

FIG. 1 shows remarkably higher accumulation in lung for the formulation (siRNA GST-π, Compound A 25 mol %, cholesterol 30 mol %, DOPE 20 mol %, DOPC 20 mol %, DSPE-mPEG-2000 5 mol %) as compared to a similar formulation using DMPE-mPEG-2000 lipid compound. The combination of Compound A with the DSPE lipid compound in a nanoparticle liposomal formulation provided surprisingly enhanced accumulation of the GST-π siRNA in lung.

DETAILED DESCRIPTION

Figure 1:
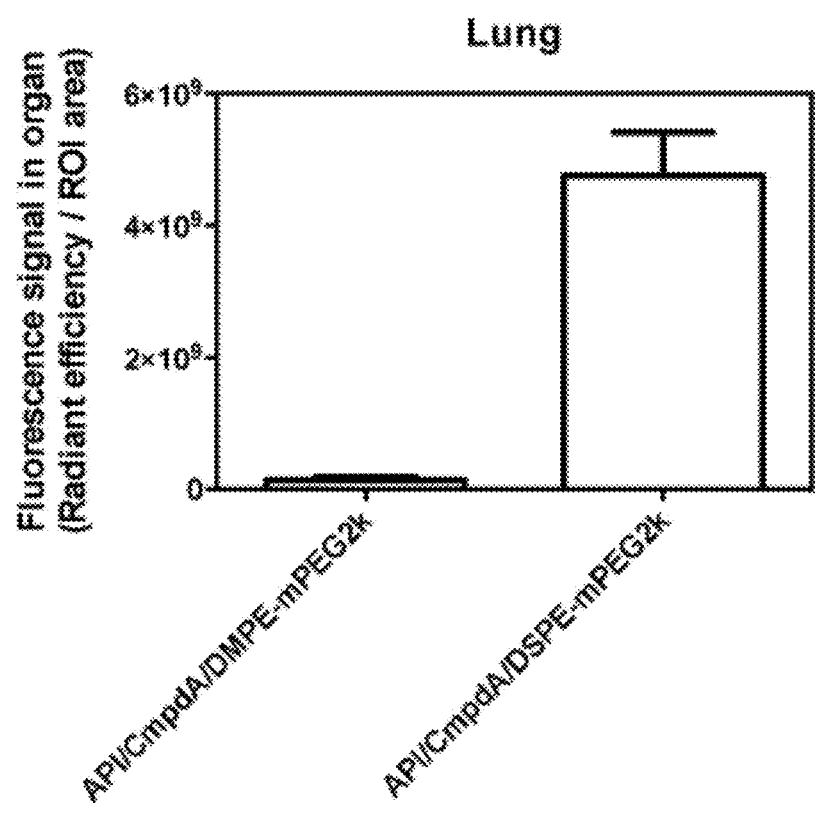
FIG. 1 shows enhanced distribution to lung in vivo mouse using a pharmaceutical formulation of this invention containing a siRNA targeted to GST-π, an ionizable lipid Compound A, and a DSPE lipid compound.

Various embodiments of this invention provide compounds and compositions for use in therapeutic formulations for delivery to malignant tumors. In some aspects, this invention relates to compounds, compositions and methods for providing nanoparticles to deliver and distribute active agents to malignant tumor cells, as well as tissues, organs, and subjects having malignant tumors.

Various embodiments of this invention provide a formulation designed for clinical use containing an active nucleic acid API (such as an active siRNA) agent that can decrease expression of a GST-π nucleic acid molecule.

Embodiments of a pharmaceutical composition of this invention may contain an ionizable lipid of the Formula I or II (such as Compound A) for delivering the active nucleic acid API (e.g., siRNA) to cells of malignant tumors. The ionizable lipid of the Formula I or II (e.g., Compound A), along with additional lipid components in a formulation of this invention can be used to form nanoparticles to deliver and distribute the active nucleic acid API (e.g., siRNA) for treating or ameliorating malignant tumors.

Embodiments of a pharmaceutical composition of this invention can contain a 1,2-distearoyl-sn-glycero-3-phosphoethanolamine (DSPE) lipid compound for delivering the active nucleic acid API (e.g., siRNA) to cells of malignant tumors. The DSPE lipid compound, which can be DSPE-mPEG-2000, along with additional lipid components in a formulation of this invention can be used to form nanoparticles to deliver and distribute the active nucleic acid API (e.g. siRNA) for treating or ameliorating malignant tumors.

In some embodiments, a pharmaceutical composition of this invention containing an active agent that is a siRNA target to GST-π, along with an ionizable lipid of the Formula I or II (e.g., Compound A) and a DSPE-mPEG-2000 lipid component, can exhibit enhanced distribution of the active agent to lung by parenteral administration.

Embodiments of this invention include a pharmaceutical solution of a pharmaceutical composition, which is suitable for lyophilization. A pharmaceutical solution of a pharmaceutical composition may contain solvents, for example, ethanol and water for injection, as well as protective agents, for example, sucrose and 2-hydroxypropyl-β-cyclodextrin, which protect the active agent during lyophilization. A pharmaceutical solution can also contain a buffer. A pharmaceutical solution allows a suspension of a pharmaceutical composition to be made, which can be maintained during lyophilization.

In further embodiments, this invention includes a solid lyophile composition made from a pharmaceutical solution. The pharmaceutical solution can be lyophilized to a solid cake or powder, which maintains the activity of the active agent of the pharmaceutical solution.

Various embodiments of a solid lyophile composition of this invention can be prepared in a vial or other container for use as a drug product. A kit utilizing the vial of the solid lyophile composition can contain instructions for using the drug product, and for preparing a reconstituted drug from the solid lyophile composition.

In further embodiments, an active agent of this invention can be delivered using a reconstituted form of a solid lyophile composition. The reconstituted solution form of a solid lyophile composition, which may be prepared with a sterile diluent, can be used as a drug for parenteral delivery.

In another aspect, embodiments of this invention provide methods for utilizing therapeutic compositions that decrease the expression of a GST-π nucleic acid molecule or polypeptide, for the treatment of a neoplasia in a subject, wherein the neoplasia is associated with cells containing a KRAS mutation or displaying aberrant KRAS expression levels.

The therapeutic compositions of embodiments of this invention can include an inhibitory nucleic acid molecule, such as a siRNA or shRNA.

A KRAS-associated malignant tumor or KRAS-associated cancer is defined herein as (a) a cancer cell or tumor cell containing a somatic KRAS mutation, or (b) a cancer cell or tumor cell with an abnormal expression level of KRAS including, but not limited to, amplification of the KRAS encoding DNA, or over-expression of the KRAS gene, or under-expression of the KRAS gene when compared to level found in normal, non-cancer cells.

GST-π denotes an enzyme, which is encoded by the GSTP1 gene, and catalyzes glutathione conjugation. GST-π is present in various animals, including humans, and its sequence information is known and given in NCBI database accession numbers (e.g., human: NP_000843 (NM_000852), rat: NP_036709 (NM_012577), mouse: NP_038569 (NM_013541), etc.

In an embodiment, this invention encompasses RNAi molecules for suppressing DNA encoding GST-π, and dominant negative variants of GST-π.

In general, after a subject is diagnosed as having a neoplasia, e.g., a lung cancer, associated with a KRAS mutation or a KRAS amplification, a method of treatment involving suppression of GST-π is selected.

Examples of an agent or drug that suppresses GST-π include an RNAi molecule.

Lyophilized Nanoparticle Formulations

In some aspects, delivery of an active agent in vivo can surprisingly be accomplished with a nanoparticle formulation of this invention that can be lyophilized, reconstituted, and injected intravenously.

Embodiments of this invention further provide lyophile forms of nanoparticles that can be reconstituted into effective therapeutic compositions, which can be used to deliver therapeutic nucleic acid agents for transfection.

In some aspects, this invention provides compositions and compounds for forming solutions or suspensions of therapeutic lipid nanoparticles that are stable in lyophilization processes. The therapeutic lipid nanoparticles can encapsulate nucleic acid agents, and can be transformed and stored in solid lyophile forms. The lyophile forms can be reconstituted to provide therapeutic lipid nanoparticles with encapsulated nucleic acid agents. The reconstituted lipid nanoparticles can have surprisingly advantageous transfection properties, including particle size and distribution.

Embodiments of this invention include a range of compositions and compounds for forming solutions or suspensions of therapeutic lipid nanoparticles that can undergo a lyophilization process to provide stable, solid lyophile forms for long-term storage of a nucleic acid therapeutic.

In further aspects, this invention provides compounds and methods for forming solutions or suspensions of therapeutic lipid nanoparticles that are stable in lyophilization processes. The lyophilization processes of this invention can provide stable lyophile forms of therapeutic lipid nanoparticles, in which the nanoparticles can encapsulate nucleic acid agents. The lyophile forms can be stored for a period of time, and reconstituted to provide therapeutic lipid nanoparticles with encapsulated nucleic acid agents.

In some embodiments, this invention includes a range of compositions and compounds for solutions or suspensions of lipid nanoparticles that can undergo a lyophilization process to provide stable, solid lyophile forms for long-term storage of a nucleic acid therapeutic. Compositions and processes of this invention can provide lyophile forms that can be reconstituted and provide advantageous activity, particle size, storage time, and serum stability.

In further aspects, this invention relates to compounds, compositions and methods for providing nanoparticles to deliver and distribute active agents or drug compounds to subjects, tissues, and organs.

In an embodiment, this invention provides a range of lipid compounds and ionizable compounds for delivering active agents to cells. The lipid compounds and ionizable compounds of this disclosure can be used to form nanoparticles to deliver and distribute active agents.

In an embodiment, this invention contemplates lipid nanoparticle drug formulations containing, for example, siRNA agents, which can be prepared by lyophilization of a suspension of the nanoparticles, and reconstitution of the nanoparticles into a suspension.

In some embodiments, lipid nanoparticles can be synthesized by high speed injection of lipid/ethanol solution into an siRNA buffer solution. A second buffer can be diafiltered and used as an external buffer through TFF cartridges to make a final product aqueous suspension.

In some embodiments, the nanoparticles can have an average diameter of from 45 nm to 110 nm. The concentration of the nucleic acid active agents can be from 1 mg/mL to 10 mg/mL.

It was found that lipid nanoparticles can survive lyophilization of the suspension, when the suspension is made into a protected composition.

In some embodiments, a protected composition of this invention can be composed of an aqueous suspension of the lipid nanoparticles in a pharmaceutically acceptable solution, a dextrin compound, and a saccharide sugar compound. The lipid nanoparticles can encapsulate an active agent, such as one or more nucleic acid active agents.

Lyophilization of the protected suspension can provide a solid lyophile product, which can be reconstituted into a suspension of lipid nanoparticles.

The reconstituted suspension can contain lipid nanoparticles, which encapsulate the active agent and are comparable to the lipid nanoparticles before lyophilization.

In certain embodiments, the reconstituted suspension can provide activity of the encapsulated agent, which is comparable to that of the suspension before lyophilization.

In further aspects, the reconstituted suspension can provide stable nanoparticles comparable to that of the suspension before lyophilization. In certain aspects, the average particle size of the nanoparticles can be nearly equal to the size of the nanoparticles in the suspension before lyophilization.

In an embodiment, the compositions and processes of this invention can provide surprising activity and stability of a reconstituted suspension composed of nanoparticles having an encapsulated agent.

In further aspects, the protected suspension, which can be lyophilized and reconstituted, can contain a protectant composition for lyophilization. A protectant composition of this invention can be composed of a dextrin compound and a saccharide sugar compound. The total amount of the dextrin and sugar compounds may be from 2% to 20% (w/v) of the protected suspension.

In some embodiments, the dextrin compound can be from 40% to 70% (w/v) of the total amount of the dextrin and sugar compounds in the protectant composition. In certain embodiments, the dextrin compound can be from 40% to 55% (w/v) of the total amount of the dextrin and sugar compounds in the protectant composition. In further embodiments, the dextrin compound may be from 40% to 45% (w/v) of the total amount of the dextrin and sugar compounds in the protectant composition. These compositions can provide unexpectedly advantageous properties of a reconstituted nanoparticle suspension, for example, insignificant change of the nanoparticle size or activity.

In some aspects, upon lyophilization and reconstitution of a protected suspension of nanoparticles, the average size of the nanoparticles can be within 10% of their size in the original composition, before lyophilization. In certain aspects, upon lyophilization and reconstitution of a protected suspension of nanoparticles, the average size of the nanoparticles can be within 5% of their size in the original composition, before lyophilization.

This invention contemplates lipid nanoparticle drug formulations containing, for example, siRNA agents, which can be prepared by lyophilization of a suspension of the nanoparticles, and reconstitution of the nanoparticles into a suspension after a period of storage. The reconstituted suspension can provide activity of the encapsulated agent, which is comparable to that of the suspension before lyophilization.

The reconstituted suspension, prepared after a period of storage, can contain lipid nanoparticles, which encapsulate the active agent and are comparable to the lipid nanoparticles before lyophilization.

In certain embodiments, the reconstituted suspension, prepared after a period of storage, can provide activity of the encapsulated agent, which is comparable to that of the suspension before lyophilization.

In further aspects, the reconstituted suspension, prepared after a period of storage, can provide stable nanoparticles comparable to that of the suspension before lyophilization. In certain aspects, the average particle size of the nanoparticles can be nearly equal to the size of the nanoparticles in the suspension before lyophilization.

Pre-Lyophilization Lipid Nanoparticle Formulations

Embodiments of this invention can provide compositions of lipid nanoparticles, which compositions contain a protectant compound for a lyophilization process.

The lipid nanoparticles can have any composition known in the art. The lipid nanoparticles may be synthesized and loaded with encapsulated cargo by any process, including processes known in the art.

In some embodiments, the lipid nanoparticles can be prepared by a submersion injection process. Some examples of processes for lipid nanoparticles are given in US 2013/0115274.

Some examples for preparing liposomes are given in Szoka, Ann. Rev. Biophys. Bioeng. 9:467 (1980); Liposomes, Marc J. Ostro, ed., Marcel Dekker, Inc., New York, 1983, Chapter 1.

In general, lipid nanoparticles can be synthesized by mixing lipid components in an organic solvent with an aqueous buffer solution containing active nucleic acid agents. The liposomes can be sized by filtration or extrusion. The liposome suspension or solution may be further transformed by diafiltration.

A lipid nanoparticle composition embodiment of this invention, which is stabilized for a lyophilization process, may contain lipid nanoparticles that encapsulate one or more active agents, such as nucleic acid agents, in a suspension. The suspension can be aqueous, and may contain a water-miscible solvent, such as ethanol. The composition, which is stabilized for a lyophilization process, may further contain protectant compounds to stabilize the liposomes in the lyophilization process.

The average size of lipid nanoparticles as synthesized can be from 40 nm to 120 nm, from 45 nm to 110 nm, from 45 nm to 80 nm, or from 45 nm to 65 nm.

The concentration of the active agent in a lipid nanoparticle composition of this invention can range from about 0.1 mg/mL to about 10 mg/mL. In some embodiments, the concentration of the active agent in a lipid nanoparticle composition of this invention can be from 0.5 mg/mL to 8 mg/mL, or from 1 mg/mL to 6 mg/mL, or from 2 mg/mL to 5 mg/mL, or from 3 mg/mL to 4 mg/mL.

Examples of protectant compounds include dextrin compounds.

Examples of dextrin compounds include maltodextrins, and beta- and gamma-cyclodextrins.

Examples of dextrin compounds include methylated beta- and gamma-cyclodextrin compounds, and sulfoalkyl ether beta- and gamma-cyclodextrin compounds.

Examples of dextrin compounds include cyclodextrin compounds having one or more of the 2, 3 and 6 hydroxyl positions substituted with sulfoalkyl, benzenesulfoalkyl, acetoalkyl, hydroxyalkyl, hydroxyalkyl succinate, hydroxyalkyl malonate, hydroxyalkyl glutarate, hydroxyalkyl adipate, hydroxyalkyl, hydroxyalkyl maleate, hydroxyalkyl oxalate, hydroxyalkyl fumarate, hydroxyalkyl citrate, hydroxyalkyl tartrate, hydroxyalkyl malate, or hydroxyalkyl citraconate groups.

Examples of dextrin compounds include (2-hydroxypropyl)-β-cyclodextrin, 2-hydroxypropyl-3-cyclodextrin succinate, (2-hydroxypropyl)-γ-cyclodextrin, and 2-hydroxypropyl-γ-cyclodextrin succinate.

Examples of dextrin compounds include hydroxyethyl 3-cyclodextrin.

Examples of dextrin compounds include dimethyl 3-cyclodextrin and trimethyl 3-cyclodextrin.

Examples of dextrin compounds include sulfobutyl ether 3-cyclodextrin and sulfobutyl ether γ-cyclodextrin.

Examples of dextrin compounds include methyl-3-cyclodextrin and methyl-γ-cyclodextrin.

Examples of dextrin compounds include hydroxypropyl-sulfobutyl-3-cyclodextrin.

Examples of dextrin compounds include H107 SIGMA cyclodextrin (Sigma-Aldrich Corp.).

Examples of dextrin compounds include CAVAMAX, CAVASOL, and CAVATRON cyclodextrins (Ashland Inc.).

Examples of dextrin compounds include KLEPTOSE and CRYSMEB cyclodextrins (Roquette America Inc.).

Examples of dextrin compounds include CAPTISOL cyclodextrins (Ligand Pharmaceuticals, Inc.).

In some embodiments, examples of dextrin compounds include dextrin compounds attached to a polymer chain or network. For example, cyclodextrin molecules can be attached to polymers of polyacrylic acid. In further embodiments, cyclodextrin molecules can be linked together with cross linking compounds such as acryloyl groups. In certain embodiments, vinyl acrylate hydrogel forms with attached cyclodextrin compounds can be used.

In some aspects, a dextrin compound to be used in a lipid nanoparticle composition of this invention can be combined with an adsorbate compound before being introduced into the lipid nanoparticle composition. Without wishing to be bound by any one particular theory, the pre-adsorption of a sterol compound by the dextrin compound may form an inclusion complex that can prevent a loss of activity of the active agent in the reconstituted drug product.

Examples of adsorbate compounds include cholesterol, lanosterol, zymosterol, zymostenol, desmosterol, stigmastanol, dihydrolanosterol, 7☐dehydrocholesterol.

Examples of adsorbate compounds include pegylated cholesterols, and cholestane 3☐oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of adsorbate compounds include phytosterols, beta-sitosterol, campesterol, ergosterol, brassicasterol, delta-7-stigmasterol, and delta-7-avenasterol.

Additional examples of protectant compounds include saccharide compounds. Examples of saccharide compounds include sugar compounds.

Examples of protectant sugar compounds include monosaccharides such as C(5-6) aldoses and ketoses, as well as disaccharides such as sucrose, lactose, lactulose, maltose, trehalose, cellobiose, kojibiose, sakebiose, isomaltose, sophorose, laminaribiose, gentiobiose, turanose, maltulose, isomaltulose, gentiobiulose, mannobiose, melibiose, melibiulose, and xylobiose.

Examples of protectant saccharide compounds include polysaccharides such as ficoll.

The concentration of protectant compounds in the pre-lyophilization formulation can be from about 1% (w/v) to about 25% (w/v).

In some embodiments, the concentration of protectant compounds in the pre-lyophilization formulation can be from 2% (w/v) to 20% (w/v), or from 4% (w/v) to 16% (w/v), or from 5% (w/v) to 15% (w/v), or from 6% (w/v) to 14% (w/v), or from 8% (w/v) to 12% (w/v).

In certain embodiments, the concentration of protectant compounds in the pre-lyophilization formulation can be 6% (w/v), or 8% (w/v), or 10% (w/v), or 12% (w/v), or 14% (w/v), or 16% (w/v), or 18% (w/v), or 20% (w/v), or 22% (w/v), or 24% (w/v).

Lyophilization Processes

Lyophilization processes can be carried out in any suitable vessel, such as glass vessels, or, for example, glass vials, or dual-chamber vessels, as are known in the pharmaceutical arts.

A stabilized lipid nanoparticle composition of this invention containing a protectant compound can be introduced into to the glass vessel. The volume of the composition added to the vessel can be from 0.1-20 mL, or from 1-10 mL.

Any lyophilization process can be used, including those known in the pharmaceutical arts. See, e.g., Remington's Pharmaceutical Sciences, 18th Ed., Mack Publishing Co., Easton, Pa. (1990).

The lyophilization process can include freezing the protectant-stabilized lipid nanoparticle composition at a temperature of from about −40° C. to about −30° C. The frozen composition can be dried form a lyophilized composition.

In some embodiments, the freezing step can ramp the temperature from ambient to the final temperature over several minutes. The temperature ramp can be about 1° C./minute.

In some embodiments, the drying step can be performed at a pressure in a range of about 0-250 mTorr, or 50-150 mTorr, at a temperature of from about −15° C. to about −38° C. The drying step can be continued at a higher temperature, up to ambient temperature, over a period of up to several days. The level of residual water in the solid lyophile can be less than about 5%, or less than 4%, or less than 3%, or less than 2%, or less than 1% (w/v).

The protectant-stabilized lipid nanoparticle compositions of embodiments of this invention, after lyophilization, can be reconstituted by methods known in the pharmaceutical arts.

In some aspects, this invention provides methods for inhibiting the level of aggregated particles in a reconstituted drug product, made from a protectant-stabilized lipid nanoparticle composition of this invention after lyophilization.

In some embodiments, the reconstituted drug product, made from a protectant-stabilized lipid nanoparticle composition of this invention after lyophilization, can have reduced levels of aggregate particles.

In certain embodiments, the reconstituted drug product, made from a protectant-stabilized lipid nanoparticle composition of this invention after lyophilization, can have reduced levels of aggregate particles with a size greater than about 0.2 μm, or greater than about 0.5 μm, or greater than about 1 μm.

Reconstituted Drug Product

The lyophile can be reconstituted in a pharmaceutically acceptable carrier.

Examples of a pharmaceutically acceptable carrier include sterile water, water for injection, sterile normal saline, bacteriostatic water for injection, and a nebulizer solution.

Examples of a pharmaceutically acceptable carrier include a pharmaceutically acceptable solution.

Examples of a pharmaceutically acceptable solution include HEPES buffer, phosphate buffers, citrate buffers, and a buffer containing Tris(hydroxymethyl)aminomethane.

Examples of a pharmaceutically acceptable solutions include pharmaceutically acceptable buffer solutions.

Examples of a pharmaceutically acceptable solution include buffer solutions of maleic acid, tartaric acid, lactic acid, acetic acid, sodium bicarbonate, and glycine.

The reconstituted lyophile can be used as a drug product.

The reconstituted lyophile can be further diluted with isotonic saline or other excipients to provide a predetermined concentration for administration.

Examples of excipients include tonicifiers.

Examples of excipients include stabilizers such as human serum albumin, bovine serum albumin, a-casein, globulins, a-lactalbumin, LDH, lysozyme, myoglobin, ovalbumin, and RNase A.

Examples of excipients include buffers such as potassium acetate, sodium acetate, and sodium bicarbonate.

Examples of excipients include amino acids such as glycine, alanines, arginine, betaine, leucine, lysine, glutamic acid, aspartic acid, histidine, proline, 4-hydroxyproline, sarcosine, γ-aminobutyric acid, alanopine, octopine, strombine, and trimethylamine N-oxide.

Examples of excipients include non-ionic surfactants such as polysorbate 20, polysorbate 80, and poloxamer 407.

Examples of excipients include dispersing agents such as phosphotidyl choline, ethanolamine, acethyltryptophanate, polyethylene glycol, polyvinylpyrrolidone, ethylene glycol, glycerin, glycerol, propylene glycol, sorbitol, xylitol, dextran, and gelatin.

Examples of excipients include antioxidants such as ascorbic acid, cysteine, thioglycerol, thioglycolic acid, thiosorbitol, and glutathione.

Examples of excipients include reducing agents such as dithiothreitol, thiols, and thiophenes.

Examples of excipients include chelating agents such as EDTA, EGTA, glutamic acid, and aspartic acid.

In some embodiments, the lyophile can be reconstituted using a syringe needle through a stoppered vial. The lyophile can be reconstituted with or without shaking the vial.

The time for reconstitution can be from 3-30 seconds, or longer.

In some embodiments, the reconstituted nucleic acid drug product can have less than 0.001% (w/v) of aggregate particles with a size greater than 0.2 μm.

In certain aspects, the reconstituted nucleic acid drug product can have reduced cytokine activation.

In additional aspects, the nucleic acid drug product can be reconstituted after a storage time period of six months and retain 80% activity of the nucleic acid agents.

In some embodiments, the nucleic acid drug product can be reconstituted after a storage time period of six months and the average particle size of the lipid nanoparticles can be less than 25% greater than before lyophilization.

In certain embodiments, the nucleic acid drug product can be reconstituted after a storage time period of 24 months and retain 90% activity of the nucleic acid agents.

In further embodiments, the nucleic acid drug product can be reconstituted after a storage time period of 24 months and the average particle size of the lipid nanoparticles can be less than 25% greater than before lyophilization.

RNAi Molecules

One of ordinary skill in the art would understand that a reported sequence may change over time and to incorporate any changes needed in the nucleic acid molecules herein accordingly.

Embodiments of this invention can provide compositions and methods for gene silencing of GST-π expression using nucleic acid molecules.

Embodiments of this invention can provide compositions and methods for gene silencing of a combination of GST-π expression using nucleic acid molecules.

Examples of nucleic acid molecules capable of mediating RNA interference include molecules active in RNA interference (RNAi molecules), including a duplex RNA such as an siRNA (small interfering RNA), miRNA (micro RNA), shRNA (short hairpin RNA), ddRNA (DNA-directed RNA), piRNA (Piwi-interacting RNA), saRNA (small activating RNA), or rasiRNA (repeat associated siRNA), and modified forms thereof.

The composition and methods disclosed herein can also be used in treating various kinds of malignant tumors in a subject.

The nucleic acid molecules and methods of embodiments of this invention may be pooled, or used in combination to down regulate the expression of genes that encode GST-π.

The compositions and methods of embodiments of this invention can include one or more nucleic acid molecules, which can modulate or regulate the expression of GST-π proteins and/or genes encoding the proteins that are associated with the maintenance and/or development of diseases, as well as conditions or disorders associated with GST-π, such as malignant tumor.

The compositions and methods of embodiments of this invention are described with reference to exemplary sequences of GST-π. A person of ordinary skill in the art would understand that various aspects and embodiments of the invention are directed to any related GST-π genes, sequences, or variants, such as homolog genes and transcript variants, and polymorphisms, including single nucleotide polymorphism (SNP) associated with any GST-π genes.

In some embodiments, the compositions and methods of this invention can provide a double-stranded short interfering nucleic acid (siRNA) molecule that downregulates the expression of a GST-π gene, for example human GST-π.

A RNAi molecule of this invention can be targeted to GST-π, and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of embodiments of this invention include RNAi molecules that are active against any portion of GST-π mRNA. The RNAi molecule can include a sequence complementary to any mRNA encoding a GST-π sequence.

In some embodiments, a RNAi molecule of this disclosure can have activity against GST-π RNA, where the RNAi molecule includes a sequence complementary to an RNA having a variant GST-π encoding sequence, for example, a mutant GST-π gene known in the art to be associated with malignant tumor.

In further embodiments, a RNAi molecule of this invention can include a nucleotide sequence that can mediate silencing of GST-π gene expression.

Examples of RNAi molecules of embodiments of this invention targeted to GST-π mRNA are shown in Table 1.

TABLE 1

RNAi molecule sequences for GST-π

| SEQ ID NO | SENSE STRAND (5'-->3') SEQ ID NOS: 1 to 26 | SEQ ID NO | ANTISENSE STRAND (5'-->3') SEQ ID NOS: 27 to 52 |
|---|---|---|---|
| 1 | GAAGCCUUUUGAGACCCUANN | 27 | UAGGGUCUCAAAAGGCUUCNN |
| 2 | GAAGCCUUUUGAGACCCUA<u>UU</u> | 28 | UAGGGUCUCAAAAGGCUUC<u>UU</u> |
| 3 | GAAGCCUUUUGAGACCCUA<u>UU</u> | 29 | uagggucuCAAAAGGCUUC<u>UU</u> |
| 4 | GAAGCCUUUUGAGACCCUA<u>UU</u> | 30 | UagggucuCAAAAGGCUUC<u>UU</u> |
| 5 | GAAGCCUUUUGAGACCCUA<u>UU</u> | 31 | UAgggucuCAAAAGGCUUC<u>UU</u> |
| 6 | GAAGCCUUUUGAGACCCUA<u>UU</u> | 32 | UAGgucuCAAAAGGCUUC<u>UU</u> |
| 7 | GAAGCCUUUUGAGACCCUA<u>UU</u> | 33 | UAGGgucuCAAAAGGCUUC<u>UU</u> |
| 8 | GAAGCCUUUUGAGACCCUA<u>UU</u> | 34 | uAgGgUcUCAAAAGGCUUC<u>UU</u> |
| 9 | GAAGCCUUUUGAGACCCUA<u>UU</u> | 35 | UAgGgUcUCAAAAGGCUUC<u>UU</u> |
| 10 | GAAGCCUUUUGAGACCCUA<u>UU</u> | 36 | UaGgGuCuCAAAAGGCUUC<u>UU</u> |
| 11 | GAAGCCUUUUGAGACCCUA<u>UU</u> | 37 | UAGgGuCuCAAAAGGCUUC<u>UU</u> |
| 12 | GAAGCCUUUUGAGACCCUAtt | 38 | UagggucuCAAA<u>GGCUUC</u><u>UU</u> |

TABLE 1-continued

RNAi molecule sequences for GST-π

| SEQ ID NO | SENSE STRAND (5'-->3') SEQ ID NOS: 1 to 26 | SEQ ID NO | ANTISENSE STRAND (5'-->3') SEQ ID NOS: 27 to 52 |
|---|---|---|---|
| 13 | GAAGCCUUUUGAGACCCUA<u>AUU</u> | 39 | UAGGGUCUCAAAAGGCUUC<u>UU</u> |
| 14 | GAAGCCUUUUGAGACCCUA<u>UU</u> | 40 | fUAGGGUCUCAAAAGGCUUC<u>UU</u> |
| 15 | GAAGCCUUUUGAGACCCUA<u>UU</u> | 41 | uAGGGUCUCAAAAGGCUUC<u>UU</u> |
| 16 | GAAGCCUUUUGAGACCCUA<u>UU</u> | 42 | UsAGGGUCUCAAAAGGCUUC<u>UU</u> |
| 17 | GAAGCCUUUUGAGACCCUfA<u>UU</u> | 43 | fUAGGGUCUfCAAAAGGCfUUC<u>UU</u> |
| 18 | GAAGCCUUUUGAGfACCCUfA<u>UU</u> | 44 | fUAGGGUCUfCAfAfAAGGCfUUC<u>UU</u> |
| 19 | GAAGCCUUUUGAGACCCUA<u>UU</u> | 45 | UAGGGUCU<u>C</u>AAAAGGC<u>UU</u>C<u>UU</u> |
| 20 | GAAGCCUUUUGAGACCCUA<u>UU</u> | 46 | fUAGGGUCU<u>C</u>AAAAGGC<u>UU</u>C<u>UU</u> |
| 21 | <u>GAA</u>GCCUUUUGAGACCCUA<u>UU</u> | 47 | UAGGGUCUCAAAAGGCUUC<u>UU</u> |
| 22 | <u>GAA</u>GCCU<u>UUU</u>GAGACCC<u>U</u>A<u>UU</u> | 48 | UAGgGuCuCAAAAGGCUUC<u>UU</u> |
| 23 | <u>GAA</u>GCCU<u>UUU</u>GAGACCC<u>U</u>A<u>UU</u> | 49 | UAGgGuCu<u>C</u>AAAAGGCUUC<u>UU</u> |
| 24 | <u>GAA</u>GCCU<u>UUU</u>GAGACCC<u>U</u>A<u>UU</u> | 50 | UAGgGuCu<u>C</u>AAAAGGCUUC<u>UU</u> |
| 25 | <u>GAA</u>GCCU<u>UUU</u>GAGACCC<u>U</u>A<u>UU</u> | 51 | UAGgGuCu<u>C</u>AAAAGGC<u>UU</u>C<u>UU</u> |
| 26 | <u>GAA</u>GCCU<u>UUU</u>GAGACCC<u>U</u>A<u>UU</u> | 52 | fUAGgGuCu<u>C</u>AAAAGGC<u>UU</u>C<u>UU</u> |

Key for Table 1: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively.
Underlining refers to 2'-OMe-substituted, e.g., <u>U</u>. The lower case letter f refers to 2'-deoxy-2'-fluoro substitution, e.g. fU is 2'-deoxy-2'-fluoro-U. The lower case letter s refers to a phosphorothioate linkage. N is A, C, G, U, <u>U</u>, a, c, g, u, t, or a modified, inverted, or chemically modified nucleotide.

In further aspects, a nucleic acid molecule of an embodiment of this invention can have each strand of the molecule being from 18 to 22 nucleotides in length. A nucleic acid molecule can have a duplex region of 19 nucleotides in length.

In certain embodiments, a nucleic acid molecule can have a polynucleotide sense strand and the polynucleotide antisense strand that are connected as a single strand, and form a duplex region connected at one end by a loop.

The nucleic acid molecules of embodiments of this invention can have a blunt end, and can have one or more 3' overhangs.

The nucleic acid molecules of embodiments of this invention can be RNAi molecules that are active for gene silencing, for example, a dsRNA that is active for gene silencing, a siRNA, a micro-RNA, or a shRNA active for gene silencing, as well as a DNA-directed RNA (ddRNA), a Piwi-interacting RNA (piRNA), and a repeat associated siRNA (rasiRNA).

This invention further contemplates compositions containing one or more inventive nucleic acid molecules and a pharmaceutically acceptable carrier. The carrier can be a lipid molecule or liposome.

In some embodiments, this invention provides a range of nucleic acid molecules, wherein: a) the molecule has a polynucleotide sense strand and a polynucleotide antisense strand; b) each strand of the molecule is from 15 to 30 nucleotides in length; c) a contiguous region of from 15 to 30 nucleotides of the antisense strand is complementary to a sequence of an mRNA encoding GST-π; d) at least a portion of the sense strand is complementary to at least a portion of the antisense strand, and the molecule has a duplex region of from 15 to 30 nucleotides in length.

In some embodiments, the nucleic acid molecule can have contiguous region of from 15 to 30 nucleotides of the antisense strand that is complementary to a sequence of an mRNA encoding GST-π is located in the duplex region of the molecule.

In additional embodiments, the nucleic acid molecule can have a contiguous region of from 15 to 30 nucleotides of the antisense strand that is complementary to a sequence of an mRNA encoding GST-π.

In certain embodiments, each strand of the nucleic acid molecule can be from 18 to 22 nucleotides in length. The duplex region of the nucleic acid molecule can be 19 nucleotides in length.

In alternative forms, the nucleic acid molecule can have a polynucleotide sense strand and a polynucleotide antisense strand that are connected as a single strand, and form a duplex region connected at one end by a loop.

Some embodiments of a nucleic acid molecule of this disclosure can have a blunt end. In certain embodiments, a nucleic acid molecule can have one or more 3' overhangs.

Embodiments of this invention provide a range of nucleic acid molecules that are RNAi molecules active for gene silencing. The inventive nucleic acid molecules can be a dsRNA, a siRNA, a micro-RNA, or a shRNA active for gene silencing, as well as a DNA-directed RNA (ddRNA), Piwi-interacting RNA (piRNA), or a repeat associated siRNA (rasiRNA). The nucleic acid molecules can be active for inhibiting expression of GST-π.

Embodiments of this invention further provide nucleic acid molecules having an IC50 for knockdown of GST-π of less than 100 pM.

Additional embodiments of this invention provide nucleic acid molecules having an IC50 for knockdown of GST-π of less than 50 pM.

This invention further contemplates compositions containing one or more of the inventive nucleic acid molecules, along with a pharmaceutically acceptable carrier. In certain embodiments, the carrier can be a lipid molecule or liposome.

The compounds and compositions of embodiments of this invention are useful in methods for preventing or treating a GST-π associated disease, by administering a compound or composition to a subject in need.

As used herein, the RNAi molecule denotes any molecule that causes RNA interference, including a duplex RNA such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof. These RNAi molecules may be commercially available or may be designed and prepared based on known sequence information, etc. The antisense nucleic acid includes RNA, DNA, PNA, or a complex thereof. As used herein, the DNA/RNA chimera polynucleotide includes a double-strand polynucleotide composed of DNA and RNA that inhibits the expression of a target gene.

In one embodiment, the agents of embodiments of this invention contain siRNA as a therapeutic agent. An siRNA molecule can have a length from about 10-50 or more nucleotides. An siRNA molecule can have a length from about 15-45 nucleotides. An siRNA molecule can have a length from about 19-40 nucleotides. An siRNA molecule can have a length of from 19-23 nucleotides. An siRNA molecule of this invention can mediate RNAi against a target mRNA. Commercially available design tools and kits, such as those available from Ambion, Inc. (Austin, Tex.), and the Whitehead Institute of Biomedical Research at MIT (Cambridge, Mass.) allow for the design and production of siRNA.

Methods for Treating Malignant Tumor

Embodiments of this invention can provide RNAi molecules that can be used to down regulate or inhibit the expression of GST-π and/or GST-π proteins. In some embodiments, a RNAi molecule of this invention can be used to down regulate or inhibit the expression of GST-π and/or GST-π proteins arising from GST-π haplotype polymorphisms that may be associated with a disease or condition such as malignant tumor.

Monitoring of GST-π protein or mRNA levels can be used to characterize gene silencing, and to determine the efficacy of compounds and compositions of this invention.

The RNAi molecules of embodiments of this disclosure can be used individually, or in combination with other siRNAs for modulating the expression of one or more genes.

The RNAi molecules of embodiments of this disclosure can be used individually, or in combination, or in conjunction with other known drugs for preventing or treating diseases, or ameliorating symptoms of conditions or disorders associated with GST-π, including malignant tumor.

The RNAi molecules of embodiments of this invention can be used to modulate or inhibit the expression of GST-π in a sequence-specific manner.

The RNAi molecules of embodiments of this disclosure can include a guide strand for which a series of contiguous nucleotides are at least partially complementary to a GST-π mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by determining the level of GST-π mRNA or the level of GST-π protein in cells of affected tissue.

Treatment of malignant tumor may be characterized by non-invasive medical scanning of an affected organ or tissue.

Embodiments of this invention may include methods for preventing, treating, or ameliorating the symptoms of a disease or condition associated with GST-π in a subject in need thereof.

In some embodiments, methods for preventing, treating, or ameliorating the symptoms of malignant tumor in a subject can include administering to the subject a RNAi molecule of this invention to modulate the expression of a GST-π gene in the subject or organism.

In some embodiments, this invention contemplates methods for down regulating the expression of a GST-π gene in a cell or organism, by contacting the cell or organism with a RNAi molecule of this invention.

GST-π inhibitory nucleic acid molecules can be nucleotide oligomers that may be employed as single-stranded or double-stranded nucleic acid molecule to decrease gene expression. In one approach, the inhibitory nucleic acid molecule is a double-stranded RNA used for RNA interference (RNAi)-mediated knockdown of gene expression. In one embodiment, a double-stranded RNA (dsRNA) molecule that is active in RNA interference is made that includes from eight to twenty-five (e.g., 8, 10, 12, 15, 16, 17, 18, 19, 20, 21, 22, 23, 24, 25) consecutive nucleotides of a nucleotide oligomer of the invention. The dsRNA can be two complementary strands of RNA that have duplexed, or a single RNA strand that has self-duplexed (small hairpin (sh)RNA).

In some embodiments, dsRNAs that are active in RNA interference are about 21 or 22 base pairs, but may be shorter or longer, up to about 29 nucleotides. Double stranded RNA can be made using standard techniques, e.g., chemical synthesis or in vitro transcription. Kits are available, for example, from Ambion (Austin, Tex.) and Epicentre (Madison, Wis.).

Methods for expressing dsRNA in mammalian cells are described in Brummelkamp et al. Science 296:550-553, 2002; Paddison et al. Genes & Devel. 16:948-958, 2002; Paul et al. Nature Biotechnol. 20:505-508, 2002; Sui et al., Proc. Natl. Acad. Sci. USA 99:5515-5520, 2002; Yu et al. Proc. Natl. Acad. Sci. USA 99:6047-6052, 2002; Miyagishi et al., Nature Biotechnol. 20:497-500, 2002; and Lee et al., Nature Biotechnol. 20:500-505 2002, each of which is hereby incorporated by reference.

An inhibitory nucleic acid molecule that "corresponds" to a GST-π gene comprises at least a fragment of the double-stranded gene, such that each strand of the double-stranded inhibitory nucleic acid molecule is capable of binding to the complementary strand of the target GST-π gene. The inhibitory nucleic acid molecule need not have perfect correspondence to the reference GST-π sequence.

In one embodiment, a siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleotide sequence of the inhibitory nucleic acid molecule exhibits 1, 2, 3, 4, 5 or more mismatches.

The inhibitory nucleic acid molecules provided by embodiments of the invention are not limited to siRNAs, but include any nucleic acid molecule sufficient to decrease the expression of a GST-π nucleic acid molecule or polypeptide. The DNA sequences provided herein may be used, for example, in the discovery and development of therapeutic antisense nucleic acid molecule to decrease the expression of the encoded protein. Embodiments of the invention further provides catalytic RNA molecules or ribozymes. Such catalytic RNA molecules can be used to inhibit expression of a target nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and US 2003/0003469 A1, each of which is incorporated by reference.

In various embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., Biochemistry, 28:4929, 1989, and Hampel et al., Nucleic Acids Research, 18: 299, 1990. Those skilled in the art will recognize that what is needed in an enzymatic nucleic acid molecule is a specific substrate binding site that is complementary to one or more of the target gene RNA regions, and that it have nucleotide sequences within or surrounding that substrate binding site which impart an RNA cleaving activity to the molecule.

Suppression of a target may be determined by the expression or activity of the corresponding protein in cells being suppressed, as compared to cells in which a suppressing agent is not utilized. Expression of protein may be evaluated by any known technique; examples thereof include an immunoprecipitation method utilizing an antibody, EIA, ELISA, IRA, IRMA, a western blot method, an immunohistochemical method, an immunocytochemical method, a flow cytometry method, various hybridization methods utilizing a nucleic acid that specifically hybridizes with a nucleic acid encoding the protein or a unique fragment thereof, or a transcription product (e.g., mRNA) or splicing product of said nucleic acid, a northern blot method, a Southern blot method, and various PCR methods.

The activity of the protein may be evaluated by analyzing a known activity of the protein including binding to a protein such as, for example, Raf-1 (in particular phosphorylated Raf-1) or EGFR (in particular phosphorylated EGFR) by means of any known method such as for example an immunoprecipitation method, a western blot method, amass analysis method, a pull-down method, or a surface plasmon resonance (SPR) method.

Examples of the mutated KRAS include, but are not limited to, those having a mutation that causes constant activation of KRAS, such as a mutation that inhibits endogenous GTPase or a mutation that increases the guanine nucleotide exchange rate. Specific examples of such mutation include, but are not limited to, for example, mutation in amino acids 12, 13 and/or 61 in human KRAS (inhibiting endogenous GTPase) and mutation in amino acids 116 and/or 119 in human KRAS (increasing guanine nucleotide exchange rate) (Bos, *Cancer Res.* 1989; 49 (17): 4682-9, Levi et al., *Cancer Res.* 1991; 51 (13): 3497-502).

In some embodiments of the present invention, the mutated KRAS can be a KRAS having a mutation in at least one of amino acids 12, 13, 61, 116, and 119 of human KRAS. In one embodiment of the present invention, the mutated KRAS has a mutation at amino acid 12 of human KRAS. In some embodiments, the mutated KRAS may be one that induces overexpression of GST-π. Cells having mutated KRAS may exhibit overexpression of GST-π.

Detection of mutated KRAS may be carried out using any known technique, e.g., selective hybridization by means of a nucleic acid probe specific to a known mutation sequence, an enzyme mismatch cleavage method, sequencing (Bos, *Cancer Res.* 1989; 49 (17): 4682-9), and a PCR-RFLP method (Miyanishi et al., *Gastroenterology.* 2001; 121 (4): 865-74).).

Detection of target expression may be carried out using any known technique. Whether or not the target is being overexpressed may be evaluated by for example comparing the degree of expression of the target in cells having mutated KRAS with the degree of expression of the target in the same type of cells having normal KRAS. In this situation, the target is being overexpressed if the degree of expression of the target in cells having mutated KRAS exceeds the degree of expression of the target in the same type of cells having normal KRAS.

In one aspect, an embodiment of the invention features a vector encoding an inhibitory nucleic acid molecule of any of the above aspects. In a particular embodiment, the vector is a retroviral, adenoviral, adeno-associated viral, or lentiviral vector. In another embodiment, the vector contains a promoter suitable for expression in a mammalian cell.

The amount of active RNA interference inducing ingredient formulated in a composition of an embodiment of the present invention may be an amount that does not cause an adverse effect exceeding the benefit of administration. Such an amount may be determined by an in vitro test using cultured cells, or a test in a model animal or mammal such as a mouse, a rat, a dog, or a pig, etc., and such test methods are known to those skilled in the art. The methods of embodiments of this invention can be applicable to any animal, including humans.

The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of 2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797; Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A double stranded RNA (dsRNA) which is a Dicer substrate can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

Methods of Use of RNAi Molecules

The nucleic acid molecules and RNAi molecules of embodiments of this invention may be delivered to a cell or tissue by direct application of the molecules, or with the molecules combined with a carrier or a diluent.

The nucleic acid molecules and RNAi molecules of embodiments of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of embodiments of this invention can be packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

A inhibitory nucleic acid molecule or composition of an embodiment of this invention may be administered within a pharmaceutically-acceptable diluents, carrier, or excipient, in unit dosage form. Certain pharmaceutical practices may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, or intraperitoneal administration. For example, therapeutic formulations may be in the form of liquid solutions or suspensions.

Compositions and methods of embodiments of this disclosure can include an expression vector that includes a nucleic acid sequence encoding at least one RNAi molecule of this invention in a manner that allows expression of the nucleic acid molecule.

The nucleic acid molecules and RNAi molecules of embodiments of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct, where the dsRNA is active in RNA interference.

Lipid formulations can be administered for example by intravenous, intramuscular, or intraperitoneal injection.

Pharmaceutically acceptable formulations for administering oligonucleotides are known and can be used.

In one embodiment of the above method, the inhibitory nucleic acid molecule is administered at a dosage of about 5 mg/m$^2$/day to about 500 mg/m$^2$/day, e.g., 5, 25, 50, 100, 125, 150, 175, 200, 225, 250, 275, or 300 mg/m$^2$/day.

In some embodiments, the inhibitory nucleic acid molecules of this invention are administered systemically in dosages from about 1 mg/kg to about 100 mg/kg, e.g., 1, 5, 10, 20, 25, 50, 75, or 100 mg/kg.

In further embodiments, the dosage can range from about 25 mg/m$^2$/day to about 500 mg/m$^2$/day.

Methods known in the art for making formulations are found, for example, in "Remington: The Science and Practice of Pharmacy" Ed. A. R. Gennaro, Lippincourt Williams & Wilkins, Philadelphia, Pa., 2000. See also Remingtons Pharmaceutical Sciences, 18th Ed., Gennaro, ed., Mack Publishing Co., Easton, Pa., 1990; Goodman & Gilman, The Pharmacological Basis of Therapeutics, 9th Ed., Hardman et al., eds. McGraw-Hill, New York, N.Y., 1996.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleotide oligomer of the invention can depend on such variables as the type and extent of the disorder, the overall health status of the particular patient, the formulation of the compound excipients, and its route of administration.

All of the above methods for reducing malignant tumors may be either an in vitro method or an in vivo method. Dosage may be determined by an in vitro test using cultured cells, etc., as is known in the art. An effective amount may be an amount that reduces tumor size in KRAS associated tumors by at least 10%, at least 20%, or at least 30%, or at least 40%, or at least 50%, or at least 60%, or at least 70%, or at least 80%, or at least 90%, up to 100% of the tumor size.

A pharmaceutical composition of an embodiment of this invention can be effective in treating a KRAS associated disease. Examples of the diseases include a disease due to abnormal cell proliferation, a disease due to KRAS mutation, and a disease due to GST-π overexpression.

Examples of the disease due to abnormal cell proliferation include malignant tumors, hyperplasia, keloid, Cushing's syndrome, primary aldosteronism, erythroplakia, polycythemia vera, leukoplakia, hyperplastic scar, lichen planus, and lentiginosis.

Examples of the disease due to KRAS mutation include malignant tumor (also called a cancer or a malignant neoplasm).

Examples of the disease due to GST-π overexpression include malignant tumor.

Examples of cancer include sarcomas.

In one embodiment of the present invention, the cancer includes cancer cells having the mutated KRAS defined above. In another embodiment, the cancer includes cancer cells that exhibit hormone- or growth factor-independent proliferation. In further embodiments, a cancer includes cancer cells exhibiting GST-π overexpression.

Additional Active Agents or Drugs for Suppressing GST-π

Examples of additional active agents for inhibiting the activity of GST-pi include, but are not limited to, substances binding to GST-pi, for example, glutathione, glutathione analogs (e.g., those described in WO95/08563, WO96/40205, WO99/54346), ketoprofen, indomethacin (see, e.g., Hall et al., Cancer Res. 1989; 49 (22): 6265-8), ethacrynic acid, piriprost (see, e.g., Tew et al., Cancer Res. 1988; 48 (13): 3622-5), anti-GST-pi antibodies, and dominant negative mutants of GST-π. These agents are either commercially available or can be appropriately produced on the basis of publicly known techniques.

Formulations with Three or More Components for Delivery of Agents in Malignant Tumor As used herein, a component of a formulation, such as a "lipid," can be a single compound, or can be a combination of one or more suitable lipid compounds. For example, "a stabilizer lipid" can refer to a single stabilizer lipid, or to a combination of one or more suitable stabilizer lipids. One skilled in the art can readily appreciate that certain combinations of the compounds described herein can be used without undue experimentation, and that various combinations of compounds are encompassed by the description of a component of a formulation.

This invention can provide a composition for use in distributing an active agent in cells, tissues or organs, organisms, and subjects, where the composition includes one or more ionizable lipid molecules of this invention.

Compositions of this invention may include one or more of the ionizable lipid molecules, along with a structural lipid, and one or more lipids for reducing immunogenicity of the nanoparticles.

An ionizable lipid molecule of an embodiment of this invention can be any mol % of a composition of this invention.

The ionizable lipid molecules of a composition of embodiments of this invention can be from 15 mol % to 35 mol % of the lipid components of the composition. In certain embodiments, the ionizable lipid molecules of a composition can be from 20 mol % to 30 mol % of the lipid components of the composition.

The structural lipid of a composition of embodiments of this invention can be from 20 mol % to 50 mol % of the lipid components of the composition. In certain embodiments, the structural lipid of a composition can be from 35 mol % to 45 mol % of the lipid components of the composition.

The one or more lipids for reducing immunogenicity of the nanoparticles can be from a total of 1 mol % to 10 mol %, or 1 mol % to 8 mol % of the lipid components of the composition. In certain embodiments, the one or more lipids for reducing immunogenicity of the nanoparticles can be from a total of 1 mol % to 5 mol % of the lipid components of the composition.

In compositions of embodiments of this invention, the entirety of the lipid components may include one or more of the ionizable lipid molecular components, one or more structural lipids, and one or more lipids for reducing immunogenicity of the nanoparticles.

Formulations with Four or More Lipid Components for Delivery of Agents in Malignant Tumor This invention can provide a composition for use in distributing an active agent in cells, tissues or organs, organisms, and subjects, where the composition includes one or more ionizable lipid molecules of this invention.

Compositions of embodiments of this invention may include one or more of the ionizable lipid molecules, along with a structural lipid, one or more stabilizer lipids, and one or more lipids for reducing immunogenicity of the nanoparticles.

An ionizable lipid molecule of embodiments of this invention can be any mol % of a composition of this invention.

The ionizable lipid molecules of a composition of embodiments of this invention can be from 15 mol % to 35 mol % of the lipid components of the composition. In certain embodiments, the ionizable lipid molecules of a composition can be from 15 mol % to 25 mol %, or from 20 mol % to 30 mol % of the lipid components of the composition.

The structural lipid of a composition of embodiments of this invention can be from 25 mol % to 40 mol % of the lipid components of the composition. In certain embodiments, the structural lipid of a composition can be from 25 mol % to 35 mol %, or from 30 mol % to 40 mol % of the lipid components of the composition.

The sum of the stabilizer lipids of a composition of embodiments of this invention can be from 25 mol % to 45% mol % of the lipid components of the composition. In certain embodiments, the sum of the stabilizer lipids of a composition can be from 30 mol % to 40 mol % of the lipid components of the composition.

In certain embodiments, the sum of the one or more stabilizer lipids can be from 25 mol % to 45 mol % of the lipids of the composition, wherein each of the stabilizer lipids individually can be from 5 mol % to 40% mol %.

In certain embodiments, the sum of the one or more stabilizer lipids can be from 30 mol % to 40 mol % of the lipids of the composition, wherein each of the stabilizer lipids individually can be from 10 mol % to 30% mol %. In various embodiments, the structural lipids (e.g., cholesterol) and the stabilizer lipids (e.g., DOPC and DOPE) combined comprise 50 mol % to 85 mol % of the total lipids of the composition.

The one or more lipids for reducing immunogenicity of the nanoparticles can be from a total of 1 mol % to 10 mol %, or 1 mol % to 8 mol % of the lipid components of the composition. In certain embodiments, the one or more lipids for reducing immunogenicity of the nanoparticles can be from a total of 1 mol % to 5 mol % of the lipid components of the composition.

In compositions of this invention, the entirety of the lipid components may include one or more of the ionizable lipid molecular components, one or more structural lipids, one or more stabilizer lipids, and one or more lipids for reducing immunogenicity of the nanoparticles.

Examples of Lipid Compositions

In some embodiments, three lipid-like components, i.e. one or more ionizable molecules, a structural lipid, and one or more lipids for reducing immunogenicity of the nanoparticles can be 100% of the lipid components of the composition.

Examples of formulations of embodiments of this invention are shown in Table 2.

Ionizable Lipid-Like Molecules

Examples of on ionizable lipid include compounds having the structure shown in Formula I

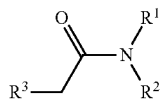

Formula I wherein $R^1$ and $R^2$ are
$R^1=CH_2(CH_2)_nOC(=O)R^4$
$R^2=CH_2(CH_2)_mOC(=O)R^5$
wherein n and m are from 1 to 2; and $R^4$ and $R^5$ are independently for each occurrence a C(12-20) alkyl group, or a C(12-20) alkenyl group having from zero to two double bonds;
wherein $R^3$ is selected from

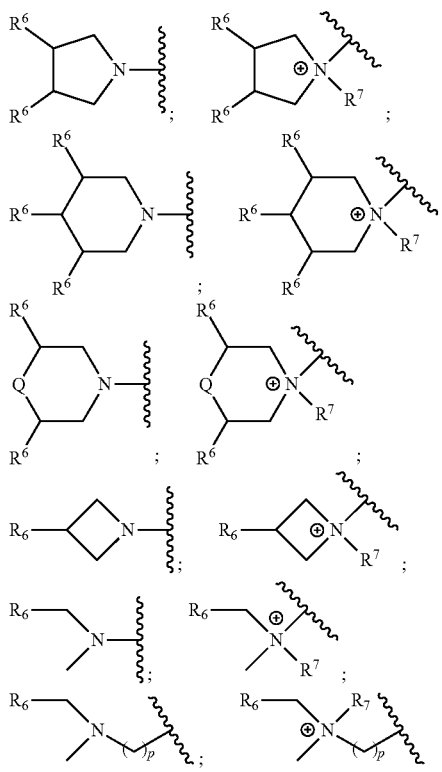

TABLE 2

Examples of pharmaceutical compositions

| No. | Cmpd A % | Cholesterol % | DOPC % | DOPE % | DSPE-mPEG % | N/P Ratio | Z-Ave (nm) | PDI | Zeta at pH 5.5 (mV) |
|---|---|---|---|---|---|---|---|---|---|
| 1 | 23.5 | 30 | 20 | 20 | 6.5 | 2.5 | 37 | 0.08 | −1.5 |
| 2 | 10 | 40 | 10 | 30 | 10 | 4 | 31 | 0.18 | −8.3 |
| 3 | 25 | 30 | 20 | 20 | 5 | 1.5 | 46 | 0.07 | −0.1 |
| 4 | 10 | 40 | 10 | 30 | 10 | 1 | 35 | 0.28 | −5.6 |
| 5 | 10 | 40 | 30 | 10 | 10 | 1 | 35 | 0.17 | −6 | wherein
R$^6$ is selected from H, alkyl, hydroxy, hydroxyalkyl, alkoxy, alkoxyalkoxy, aminoalkyl;
R$^7$ is selected from H, alkyl, hydroxyalkyl;
Q is O or NR$^7$;
p is from 1 to 4.

Examples of ionizable lipids include compounds of the following Formula II:

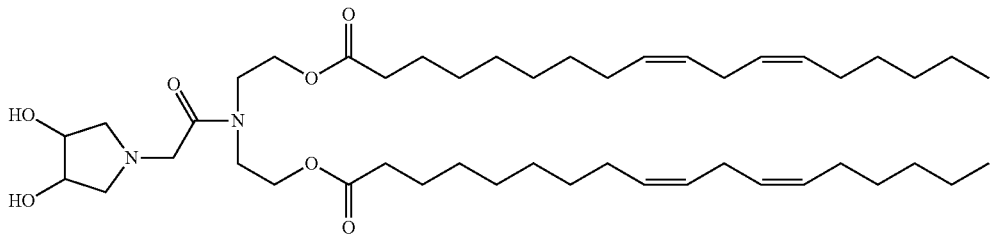

Formula II

The following Compound A, which is ((2-((3S,4R)-3,4-dihydroxypyrrolidin-1-yl)acetyl)azanediyl)bis(ethane-2,1-diyl) (9Z,9'Z,12Z,12'Z)-bis(octadeca-9,12-dienoate), is an example of an ionizable lipid of the Formula II:

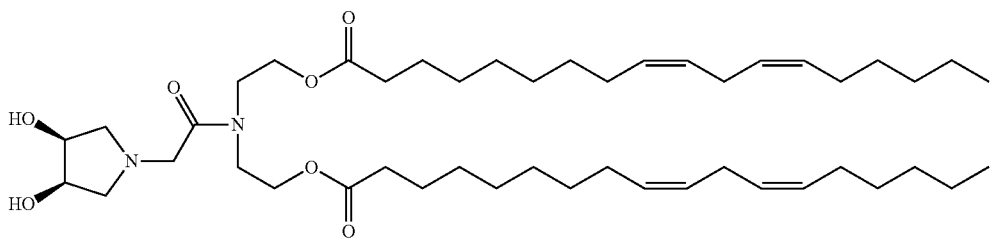

COMPOUND A

Structural Lipids

Examples of structural lipids include cholesterols, sterols, and steroids.

Examples of structural lipids include cholanes, cholestanes, ergostanes, campestanes, poriferastanes, stigmastanes, gorgostanes, lanostanes, gonanes, estranes, androstanes, pregnanes, and cycloartanes.

Examples of structural lipids include sterols and zoosterols such as cholesterol, lanosterol, zymosterol, zymostenol, desmosterol, stigmastanol, dihydrolanosterol, and 7□dehydrocholesterol.

Examples of structural lipids include pegylated cholesterols, and cholestane 3□oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of structural lipids include sterols such as phytosterols, beta-sitosterol, campesterol, ergosterol, brassicasterol, delta-7-stigmasterol, and delta-7-avenasterol.

Stabilizer Lipids

Examples of stabilizer lipids include zwitterionic lipids.

Examples of stabilizer lipids include compounds such as phospholipids.

Examples of phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and ordilinoleoylphosphatidylcholine.

Examples of stabilizer lipids include phosphatidyl ethanolamine compounds and phosphatidyl choline compounds.

Examples of stabilizer lipids include 1,2-Dioleoyl-sn-Glycero-3-Phosphocholine (DOPC).

Examples of stabilizer lipids include diphytanoyl phosphatidyl ethanolamine (DPhPE) and 1,2-Diphytanoyl-sn-Glycero-3-Phosphocholine (DPhPC).

Examples of stabilizer lipids include 1,2-distearoyl-sn-glycero-3-phosphocholine (DSPC), 1,2-dipalmitoyl-sn-glycero-3-phosphocholine (DPPC), 1,2-dipalmitoyl-sn-glycero-3-phosphoethanolamine (DPPE), and 1,2-dioleoyl-sn-glycero-3-phosphoethanolamine (DOPE).

Examples of stabilizer lipids include 1,2-dilauroyl-sn-glycerol (DLG); 1,2□dimyristoyl-sn-glycerol (DMG); 1,2-dipalmitoyl-sn-glycerol (DPG); 1,2□distearoyl-sn-glycerol (DS G); 1,2-diarachidoyl-sn-glycero-3-phosphocholine (DAPC); 1,2□dilauroyl-sn-glycero-3-phosphocholine (DLPC); 1,2□dimyristoyl-sn-glycero-3-phosphocholine (DMPC); 1,2-dipalmitoyl-sn-glycero-O-ethyl-3-phosphocholine (DPePC); 1,2□dilauroyl-sn-glycero-3-phosphoethanolamine (DLPE); 1,2-dimyristoyl-sn-glycero-3-phosphoethanolamine (DMPE); 1,2-distearoyl-sn-glycero-3-phosphoethanolamine (DSPE); 1-palmitoyl-2-linoleoyl-sn-glycero-3-phosphocholine; 1-palmitoyl-2-oleoyl-sn-glycero-3-phosphocholine (POPC); 1-palmitoyl-2-lyso-sn-glycero-3-phosphocholine (P-Lyso-PC); and 1-Stearoyl-2-lyso-sn-glycero-3-phosphocholine (S-Lyso-PC).

As used herein, the term DMPE-mPEG-2000 refers to 1,2-distearoyl-sn-glycero-3-phosphoethanolamine-N-[methoxy(polyethylene glycol)-2000].

Lipids for Reducing Immunogenicity

Examples of lipids for reducing immunogenicity include polymeric compounds and polymer-lipid conjugates.

Examples of lipids for reducing immunogenicity include pegylated lipids having polyethyleneglycol (PEG) regions. The PEG regions can be of any molecular mass. In some embodiments, a PEG region can have an average molecular mass of 200, 300, 350, 400, 500, 550, 750, 1000, 1500, 2000, 3000, 3500, 4000 or 5000 Da.

Examples of lipids for reducing immunogenicity include compounds having a methoxypolyethyleneglycol region.

Examples of lipids for reducing immunogenicity include compounds having a carbonyl-methoxypolyethyleneglycol region.

Examples of lipids for reducing immunogenicity include compounds having a multi-branched PEG region.

Examples of lipids for reducing immunogenicity include compounds having a polyglycerine region.

Examples of lipids for reducing immunogenicity include polymeric lipids such as DSPE-mPEG, DMPE-mPEG, DPPE-mPEG, and DOPE-mPEG.

Examples of lipids for reducing immunogenicity include PEG-phospholipids and PEG-ceramides.

Lipid Compositions

In some embodiments, a composition can contain the ionizable lipid of the Formula II (e.g., Compound A), the structural lipid cholesterol, the stabilizer lipids DOPC and DOPE, and the lipid for reducing immunogenicity DSPE-mPEG. In certain embodiments, the ionizable lipid of the Formula II (e.g., Compound A) can comprise 15 mol % to 35 mol %, or 15 mol % to 25 mol %, or 20 mol % to 30 mol % of the composition; the cholesterol can comprise from 25 mol % to 35 mol % of the total lipids of the composition; the DOPC and DOPE combined can comprise from 30 mol % to 50 mol % of the total lipids of the composition; the cholesterol, DOPC, and DOPE combined can comprise 50 mol % to 85 mol %, or 60 mol % to 80 mol %, or 75 mol % to 85 mol % of the composition; and DSPE-mPEG can comprise from 1 mol % to 8 mol %, or from 4 mol % to 6 mol %, or 5 mol %, of the total lipids of the composition. In various embodiments, the compound of Formula II, cholesterol, DOPC, DOPE, and DSPE-mPEG-2000 combined comprise at least 97 mol % of the total lipids of the composition. For example, in an embodiment the compound of Formula II, cholesterol, DOPC, DOPE, and DSPE-mPEG-2000 combined comprise about 100 mol % of the total lipids of the composition.

In one embodiment, the ionizable lipid of the Formula II (e.g., Compound A) can be 25 mol % of the total lipids of the composition; cholesterol can be 30 mol % of the total lipids of the composition, DOPC can be 20 mol % of the total lipids of the composition, DOPE can be 20 mol % of the total lipids of the composition; and DSPE-mPEG(2000) can be 5 mol % of the total lipids of the composition.

Nanoparticles

Embodiments of this invention can provide liposome nanoparticle compositions. The ionizable molecules of embodiments of this invention can be used to form liposome compositions, which can have a bilayer of lipid-like molecules.

A nanoparticle composition can have one or more of the ionizable molecules of this invention in a liposomal structure, a bilayer structure, a micelle, a lamellar structure, or a mixture thereof.

In some embodiments, a composition can include one or more liquid vehicle components. A liquid vehicle suitable for delivery of active agents of this invention can be a pharmaceutically acceptable liquid vehicle. A liquid vehicle can include an organic solvent, or a combination of water and an organic solvent.

Embodiments of this invention can provide lipid nanoparticles having a size of from 10 nm to 1000 nm. In some embodiments, the liposome nanoparticles can have a size of from 10 nm to 150 nm.

In certain embodiments, the liposome nanoparticles of this invention can encapsulate the RNAi molecule and retain at least 80% of the encapsulated RNAi molecules after 1 hour exposure to human serum.

As used herein, the term "encapsulate" refers to the ability of a nanoparticle to carry an active agent within its structure, or on its surface, such that the active agent is not removed by solvent or mobile phase exterior to the particle.

Pharmaceutical Compositions

This invention further contemplates methods for distributing an active agent to an organ of a subject for treating malignant tumor by administering to the subject a composition of this invention. Organs that can be treated include lung.

In some embodiments, this invention provides methods for treating a lung malignant tumor disease by administering to the subject a composition of this invention.

In further aspects, this invention provides a range of pharmaceutical formulations.

A pharmaceutical formulation herein can include an active agent, as well as a drug carrier, or a lipid of this invention, along with a pharmaceutically acceptable carrier or diluent. In general, active agents of this description include any active agents for malignant tumor, including any inhibitory nucleic acid molecules and any small molecular drugs. Examples of inhibitory nucleic acid molecules include ribozymes, antisense nucleic acids, and RNA interference molecules (RNAi molecules).

Examples of anti-malignant tumor and anti-cancer drugs include oncogenes-related factors, tumor angiogenesis factor, metastatic related factors, cytokines such as TGF-Beta, growth factor, proteinase such as MMP, caspase, and immunization suppression factor.

A pharmaceutical formulation of this invention may contain one or more of each of the following: a surface active agent, a diluent, an excipient, a preservative, a stabilizer, a dye, and a suspension agent.

Some pharmaceutical carriers, diluents and components for a pharmaceutical formulation, as well as methods for formulating and administering the compounds and compositions of this invention are described in Remington's Pharmaceutical Sciences, 18th Ed., Mack Publishing Co., Easton, Pa. (1990).

Examples of preservatives include sodium benzoate, ascorbic acid, and esters of p-hydroxybenzoic acid.

Examples of surface active agents include alcohols, esters, sulfated aliphatic alcohols.

Examples of excipients include sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, and calcium carboxymethyl cellulose.

A therapeutic formulation of this invention for the delivery of one or more molecules active for gene silencing can be administered to a mammal in need thereof. A therapeutically effective amount of the formulation and active agent, which may be encapsulated in a liposome, can be administered to a mammal for preventing or treating malignant tumor.

The route of administration may be local or systemic.

A therapeutically-effective formulation of this invention can be administered by various parenteral routes, including intravenous, intraperitoneal, intramuscular, and subcutaneous.

Routes of administration may include, for example, parenteral delivery, including intramuscular, subcutaneous, intravenous, intramedullary injections, as well as intrathecal, direct intraventricular, intraperitoneal, or intraocular injections.

The formulation can also be administered in sustained or controlled release dosage forms, including depot injections, osmotic pumps, and the like, for prolonged and/or timed, pulsed administration at a predetermined rate.

Embodiments of compositions of the present invention may be administered via various routes including parenteral routes, and examples thereof include, but are not limited to, intravenous, intramuscular, subcutaneous, local, intrapulmonary, intraarterial, intraportal, intraventricular, intramedullar, intra-lymph-node, intralymphatic, intrabrain, intrathecal, intracerebroventricular, percutaneous, and intraperitoneal routes, and it may be formulated into a dosage form suitable for each administration route. Such a dosage form and formulation method may be selected as appropriate from any known dosage forms and methods. See e.g. Hyojun Yaku-zaigaku, Standard Pharmaceutics, Ed. by Yoshiteru Watanabe et al., Nankodo, 2003.

Examples of the dosage form suitable for parenteral administration include injections such as an injectable solution, an injectable suspension, an injectable emulsion, and a ready-to-use injection. Formulations for parenteral administration may be a form such as an aqueous or nonaqueous isotonic sterile solution or suspension.

Pharmaceutical formulations for parenteral administration, e.g., by bolus injection or continuous infusion, include aqueous solutions of the active formulation in water-soluble form. Suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Formulations for injection may be presented in unit dosage form, e.g., in ampoules or in multi-dose containers, with an added preservative. The formulations may take such forms as suspensions, solutions or emulsions in oily or aqueous vehicles, and may contain formulary agents such as suspending, stabilizing and/or dispersing agents. Alternatively, the active ingredient may be in powder form for constitution with a suitable vehicle, e.g., sterile pyrogen-free water, before use.

In addition to the preparations described previously, the formulations may also be formulated as a depot preparation. Such long acting formulations may be administered by intramuscular injection. Thus, for example, the formulation may be formulated with suitable polymeric or hydrophobic materials, for example as an emulsion in an acceptable oil, or ion exchange resins, or as sparingly soluble derivatives, for example, as a sparingly soluble salt.

Embodiments of compositions and formulations of this invention may also be formulated for topical delivery and may be applied to the subject's skin using any suitable process for application of topical delivery vehicle. For example, the formulation may be applied manually, using an applicator, or by a process that involves both. Following application, the formulation may be worked into the subject's skin, e.g., by rubbing. Application may be performed multiple times daily or on a once-daily basis. For example, the formulation may be applied to a subject's skin once a day, twice a day, or multiple times a day, or may be applied once every two days, once every three days, or about once every week, once every two weeks, or once every several weeks.

The formulations or pharmaceutical compositions described herein may be administered to the subject by for example parenteral routes. Examples of methods of administration include, among others, administration via injection, subcutaneously, intraperitoneally, intravenously, intramuscularly, intradermally, intraorbitally, intracapsularly, intraspinally, intrasternally, or the like, including infusion pump delivery; administration locally such as by injection.

The exact formulation, route of administration and dosage for the pharmaceutical compositions can be chosen by the individual physician in view of the patient's condition. See, e.g., Goodman & Gilman's The Pharmacological Basis of Therapeutics, $12^{th}$ Ed., Sec. 1, 2011. Typically, the dose range of the composition administered to the patient can be from about 0.5 mg/kg to about 1000 mg/kg of the patient's body weight. The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from ED50 or ID50 values, or other appropriate values derived from in vitro or in vivo studies, as qualified by toxicity studies and efficacy studies in animals.

In some embodiments, the active agent, for example API(26/52), may be administered at a dose of 0.05 mg/kg to 50 mg/kg, or 0.01 mg/kg to 5 mg/kg, or 1 mg/kg to 2.5 mg/kg bodyweight of the subject, or at a dose of 1 mg/kg, 2.5 mg/kg, or 5 mg/kg bodyweight of the subject.

In some embodiments, the active agent, for example API(26/52), may be administered weekly, biweekly, or monthly.

Methods for Preventing or Treating Malignant Tumor

Embodiments of the present invention further relate to a method for controlling the activity or growth of malignant tumors, the method including administering an effective amount of the composition to a subject in need thereof. The effective amount referred to here is, in a method for treating malignant tumor, an amount that alleviates its symptoms, or delays or stops its progression, and is preferably an amount that prevents the onset or recurrence of malignant tumor, or cures it. It is also preferably an amount that does not cause an adverse effect that exceeds the benefit from administration. Such an amount may be determined as appropriate by an in vitro test using cultured cells or by a test in a model animal or mammal such as a mouse, a rat, a dog, or a pig, and such test methods are well known to a person skilled in the art. Moreover, the dose of the active agents in the carrier and the dose of the active agents used in the method of the present invention are known to a person skilled in the art, or may be determined as appropriate by the above-mentioned tests.

The frequency of administration depends on the properties of the composition used and the above-mentioned conditions of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every other week, or every few weeks (that is, every 2, 3, 4 weeks, etc.).

In some embodiments, the present invention also relates to a method for delivering a drug to a malignant tumor cell, by utilizing a liposome nanoparticle carrier as described herein. This method includes a step of administering or adding the carrier having the nucleic acid API to be delivered carried thereon and/or encapsulated therein to a living being or a medium, for example a culture medium, containing an extracellular matrix-producing cell in the lung. These steps may be achieved as appropriate in accordance with any known method or a method described in this invention. Moreover, the above method includes a mode carried out in vitro and a mode in which a malignant tumor cell in the lung inside the body is targeted.

A therapeutically-effective formulation of embodiments of this invention can be administered by systemic delivery that can provide a broad biodistribution of the active agent.

As used herein, the term "therapeutically effective amount" refers to the amount of drug formulation effective to achieve an intended purpose.

Embodiments of this invention can provide a therapeutic formulation, which includes an inventive therapeutic molecule and a pharmaceutically-acceptable carrier, such as a liposome nanoparticle.

An effective dose of a formulation of this invention may be administered from 1 to 12 times per day, or once per week. The duration of administration can be 1, 2, 3, 4, 5, 6 or 7 days, or can be 1, 2, 3, 4, 5, 6, 8, 10 or 12 weeks.

ADDITIONAL EMBODIMENTS

A composition for use in distributing an active agent (e.g., a nucleic acid API) for a treating malignant tumor in a subject, the composition comprising an ionizable lipid, a structural lipid, and a lipid for reducing immunogenicity of the nanoparticles. The malignant tumor can be located in the lung.

The ionizable lipid can be from 15 mol % to 35 mol % of the lipids of the composition, or from 20 mol % to 30 mol % of the lipids of the composition. The structural lipid can be from 25 mol % to 40 mol % of the lipids of the composition, or from 30 mol % to 40 mol % of the lipids of the composition. The structural lipid can be a cholesterol, a sterol, or a steroid. The lipid for reducing immunogenicity of the nanoparticles can be from 1 mol % to 10 mol %, or 1 mol % to 8 mol % of the lipids of the composition. The lipid for reducing immunogenicity of the nanoparticles may have a polyethyleneglycol (PEG) region having a molecular mass from 200 to 5000 Da. The lipid for reducing immunogenicity of the nanoparticles can be DPPE-mPEG, DSPE-mPEG, DMPE-mPEG, or DOPE-mPEG.

This invention further contemplates a composition for use in distributing an active agent (e.g., a nucleic acid API) for a treating malignant tumor in a subject, the composition comprising an ionizable lipid, a structural lipid, one or more stabilizer lipids, and a lipid for reducing immunogenicity of the nanoparticles. The ionizable lipid can be from 15 mol % to 40 mol % of the lipids of the composition, or from 20 mol % to 35 mol % of the lipids of the composition. The structural lipid can be from 25 mol % to 40 mol % of the lipids of the composition, or from 30 mol % to 35 mol % of the lipids of the composition.

The sum of the one or more stabilizer lipids can be from 25 mol % to 40 mol % of the lipids of the composition, wherein each of the stabilizer lipids individually is from 5 mol % to 35% mol %. The one or more stabilizer lipids can be phosphatidyl ethanolamine compounds or phosphatidyl choline compounds.

In various embodiments, the composition can be (Compound A/cholesterol/DOPC/DOPE/DSPE-mPEG-2000) in one of the following combinations, wherein the numerals refer to the mol % concentration of the component: (25/30/30/10/5), (25/30/25/15/5), (25/30/20/20/5), (25/30/15/25/5), (25/30/10/30/5), (25/35/15/20/5), (25/35/20/15/5), (30/30/15/20/5), (30/30/20/15/5), or (35/30/15/15/5).

In some embodiments, the ionizable lipid can be of Formula II (e.g., Compound A), the structural lipid can be cholesterol, the stabilizer lipids can be DOPC and DOPE, and the lipid for reducing immunogenicity of the nanoparticles can be DSPE-mPEG-2000, wherein the lipid of Formula II (e.g., Compound A) comprises 15 to 35 mol % of the composition, wherein cholesterol, DOPC, and DOPE combined comprise 50 to 85 mol % of the composition, wherein the DSPE-mPEG-2000 comprises from 1 to 8 mol % of the composition, and wherein the lipid of Formula II (e.g., Compound A), cholesterol, DOPC, DOPE, and the DSPE-mPEG-2000 combined comprise substantially 100 mol % of the lipids of the composition.

The active agent (e.g., a nucleic acid API) can be RNAi molecules targeted to GST-π. In some embodiments, the composition comprises liposome nanoparticles that encapsulate the RNAi molecules.

This invention also contemplates pharmaceutical compositions comprising a lipid composition and an active agent (e.g., a nucleic acid API). The active agent can be one or more RNAi molecules. The RNAi molecules for treating malignant tumor can include RNAi molecules targeted to GST-π. The RNAi molecules for treating malignant tumor can be, for example, siRNAs, shRNAs, or micro-RNAs, as well as DNA-directed RNAs (ddRNA), Piwi-interacting RNAs (piRNA), and repeat associated siRNAs (rasiRNA).

In certain embodiments, this invention provides a pharmaceutical composition containing RNAi molecules for treating malignant tumor that are RNAi molecules targeted to only GST-π.

The administration can be a dose of from 0.01 mg/kg to 2 mg/kg of the RNAi molecules at least once per day for a period up to twelve weeks. The administration can provide a mean AUC(0-last) of from 1 ug*min/mL to 1000 ug*min/mL and a mean $C_{max}$ of from 0.1 ug/mL to 50 ug/mL for the GST-π RNAi molecule.

This invention provides methods for preventing, treating or ameliorating one or more symptoms of a malignant tumor in a mammal in need thereof, or any animal, the method comprising administering to the mammal a therapeutically effective amount of a composition comprising RNAi molecules, wherein at least a portion of the RNAi molecules are active in reducing expression of GST-π. In some embodiments, the malignant tumor is associated with KRAS mutation in the mammal, the method further comprising identifying a tumor cell in the mammal, the tumor cell comprising at least one of: (i) a mutation of the KRAS gene, and (ii) an aberrant expression level of KRAS protein.

The methods of this invention can be applicable to any animal, including humans.

The mammal can be a human, the GST-π can be a human GST-π. The RNAi molecules can decrease expression of GST-π in the mammal. The administration can decrease expression of GST-π in the mammal by at least 5% for at least 5 days. The method can reduce one or more symptoms of the malignant tumor, or delays or terminates the progression of the malignant tumor, or reduce growth of malignant tumor cells in the subject. The tumor cells may comprise increased levels of expression of wild type KRAS protein as compared to that in a normal cell. The tumor cells may overexpress wild-type GST-π RNA or protein.

In some embodiments, the tumor cells can comprise mutations in the KRAS protein at one or more of residues 12, 13 and 61. In certain embodiments, the tumor cells can comprise mutations in the KRAS protein and the tumor is a lung cancer. The tumor can be a sarcoma, a lung adenocarcinoma. The malignant tumor can be a sarcoma, a lung adenocarcinoma.

In another aspect, embodiments of this invention relate to the surprising discovery that malignant tumor size can be reduced in vivo by treatment with siRNA inhibitors of GST-π. In addition, embodiments of this invention provide the unexpectedly advantageous result that tumor cell apoptosis can be increased to a level of synthetic lethality to provide methods and compositions for preventing or treating malignant tumors.

Embodiments of this invention relate to methods and compositions incorporating nucleic acid based therapeutic compounds for use in delivery to various organs for preventing, treating, or ameliorating conditions and diseases of malignant tumor. In some embodiments, this invention provides compositions of RNA interference molecules (RNAi molecules) for gene silencing of various targets related to malignant tumors.

Embodiments of this invention can provide compositions for delivery of therapeutic molecules, as well as methods of use thereof. Various RNA-based and drug compositions of this invention can be used in methods for preventing or treating malignant tumors.

In some embodiments, malignant tumors containing a KRAS mutation or displaying aberrant KRAS expression levels can be reduced by treatment with siRNA agents that modulate expression of GST-π to a level that creates synthetic lethality for tumor cells.

Embodiments of this invention relate to methods and compositions for nucleic acid based therapeutic compounds against malignant tumors. In some embodiments, this invention provides RNAi molecules, structures and compositions that can silence expression of GST-π. The structures and compositions of embodiments of this disclosure can be used in preventing, treating or reducing the size of malignant tumors.

Embodiments of this invention provide compositions and methods that may be used for treating a neoplasia in a subject. In particular, embodiments of this invention provides therapeutic compositions that can decrease the expression of a GST-π nucleic acid molecule or polypeptide for treating a KRAS-associated neoplasia.

In some aspects, this invention includes an inhibitory nucleic acid molecule that corresponds to, or is complementary to at least a fragment of a GST-π nucleic acid molecule, and that decreases GST-π expression in a cell.

In certain embodiments, this invention provides double-stranded nucleic acid molecules that are RNAi molecules such as siRNAs or shRNAs, as well as DNA-directed RNAs (ddRNA), Piwi-interacting RNAs (piRNA), and repeat associated siRNAs (rasiRNA) for suppressing GST-π.

Embodiments of the methods of this invention can be applicable to any animal, including humans.

In some aspects, this invention includes one or more vectors encoding the inhibitory nucleic acid molecules described above. A vector can be a retroviral, adenoviral, adeno-associated viral, or lentiviral vector. In further embodiments, a vector can contain a promoter suitable for expression in a mammalian cell. Additional embodiments include cancer cells containing a KRAS mutation or displaying aberrant KRAS expression levels, which can also contain the vector, or an inhibitory nucleic acid molecule of any one of the above aspects. In further embodiments, the cells can be neoplastic cells in vivo.

In some embodiments, this invention includes methods for decreasing GST-π expression in a malignant tumor cell containing a KRAS mutation or displaying aberrant KRAS expression. Methods can include contacting the cell with an effective amount of the inhibitory nucleic acid molecules, where the inhibitory nucleic acid molecules inhibit expression of a GST-π polypeptide, thereby decreasing GST-π expression in the cell.

In additional embodiments, methods of this invention can decrease GST-π transcription or translation in malignant tumors.

In particular embodiments, this invention includes methods for decreasing GST-π expression in a malignant tumor cell, where the cell can be a human cell, a neoplastic cell, a cell in vivo, or a cell in vitro.

Embodiments of this invention can also provide methods for treating a subject having a neoplasm, where neoplasm cancer cells contain a KRAS mutation or display aberrant KRAS expression levels. Methods can involve administering to the subject an effective amount of two or more inhibitory nucleic acid molecules, where the inhibitory nucleic acid molecules reduce GST-π expression, thereby treating the neoplasm. In some embodiments, methods of this invention can decrease the size of a neoplasm, relative to the size of the neoplasm prior to treatment or without treatment.

In various embodiments, an inhibitory nucleic acid molecule can be delivered in a liposome, a polymer, a microsphere, a nanoparticle, a gene therapy vector, or a naked DNA vector.

In further aspects, this invention features methods for treating a subject, e.g. a human patient, having a neoplasm in which the neoplasm cancer cells contain a KRAS mutation or display aberrant KRAS expression levels. In certain embodiments, the methods can include administering to the subject an effective amount of inhibitory nucleic acid molecules, where the inhibitory nucleic acid molecules are antisense nucleic acid molecules, siRNAs, dsRNAs that are active for RNA interference, or a combination thereof, which inhibit expression of a GST-π polypeptide.

In certain embodiments, the neoplasm can be a malignant tumor, or lung cancer.

Structures of Lipid Tails

Embodiments of a lipid-like compound of this invention may have one or more lipophilic tails that contain one or more alkyl or alkenyl groups. Examples of lipophilic tails include C(14:1(5))alkenyl, C(14:1(9))alkenyl, C(16:1(7))alkenyl, C(16:1(9))alkenyl, C(18:1(3))alkenyl, C(18:1(5))alkenyl, C(18:1(7))alkenyl, C(18:1(9))alkenyl, C(18:1(11))alkenyl, C(18:1(12))alkenyl, C(18:2(9,12))alkenyl, C(18:2(9,11))alkenyl, C(18:3(9,12,15))alkenyl, C(18:3(6,9,12))alkenyl, C(18:3(9,11,13))alkenyl, C(18:4(6,9,12,15))alkenyl, C(18:4(9,11,13,15))alkenyl, C(20:1(9))alkenyl, C(20:1(11))alkenyl, C(20:2(8,11))alkenyl, C(20:2(5,8))alkenyl, C(20:2(11,14))alkenyl, C(20:3(5,8,11))alkenyl, C(20:4(5,8,11,14))alkenyl, C(20:4(7,10,13,16))alkenyl, C(20:5(5,8,11,14,17))alkenyl, C(20:6(4,7,10,13,16,19))alkenyl, C(22:1(9))alkenyl, C(22:1(13))alkenyl, and C(24:1(9))alkenyl.

Chemical Definitions

The term "alkyl" as used herein refers to a hydrocarbyl radical of a saturated aliphatic group, which can be of any length. An alkyl group can be a branched or unbranched, substituted or unsubstituted aliphatic group containing from 1 to 22 carbon atoms. This definition also applies to the alkyl portion of other groups such as, for example, cycloalkyl, alkoxy, alkanoyl, and aralkyl, for example.

As used herein, a term such as "C(1-5)alkyl" includes C(1)alkyl, C(2)alkyl, C(3)alkyl, C(4)alkyl, and C(5)alkyl. Likewise, for example, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

As used herein, an alkyl group may be designated by a term such as Me (methyl), Et (ethyl), Pr (any propyl group), $^n$Pr (n-Pr, n-propyl), $^i$Pr (i-Pr, isopropyl), Bu (any butyl group), $^n$Bu (n-Bu, n-butyl), $^i$Bu (i-Bu, isobutyl), $^s$Bu (s-Bu, sec-butyl), and $^t$Bu (t-Bu, tert-butyl).

The term "alkenyl" as used herein refers to hydrocarbyl radical having at least one carbon-carbon double bond. An alkenyl group can be branched or unbranched, substituted or unsubstituted hydrocarbyl radical having 2 to 22 carbon atoms and at least one carbon-carbon double bond.

The term "substituted" as used herein refers to an atom having one or more substitutions or substituents which can be the same or different and may include a hydrogen substituent. Thus, the terms alkyl, cycloalkyl, alkenyl, alkoxy, alkanoyl, and aryl, for example, refer to groups which can include substituted variations. Substituted variations include linear, branched, and cyclic variations, and groups having a substituent or substituents replacing one or more hydrogens attached to any carbon atom of the group.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, March's Advanced Organic Chemistry, 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

EXAMPLES

Example 1

A pharmaceutical formulation embodiment of this invention having a siRNA targeted to GST-π exhibited enhanced distribution to lung in vivo.

FIG. 1 shows enhanced distribution to lung in vivo mouse (non-tumor bearing animals) using a pharmaceutical formulation of this invention containing a siRNA targeted to GST-π, an ionizable lipid Compound A, and a DSPE-mPEG-2000 lipid compound. Organs were harvested 4 hours after injection of a dose at 4 mg/kg in naïve animals, with 5 animals per group. The accumulation of siRNA in the organ was measured by fluorescence.

FIG. 1 shows remarkably higher accumulation in lung for the formulation (siRNA GST-π, Compound A 25 mol %, cholesterol 30 mol %, DOPE 20 mol %, DOPC 20 mol %, DSPE-mPEG-2000 5 mol %) as compared to a similar formulation using a DMPE-mPEG-2000 lipid compound. The combination of Compound A with the DSPE-mPEG-2000 lipid compound in a nanoparticle liposomal formulation provided surprisingly enhanced accumulation of the GST-π siRNA in lung.

Example 2

A pharmaceutical formulation embodiment of this invention having a siRNA targeted to GST-π exhibited profound reduction of tumor volume in vivo. The GST-π siRNA provided gene knockdown potency in vivo when administered in a liposomal formulation to the cancer xenograft tumors.

Figure 2:
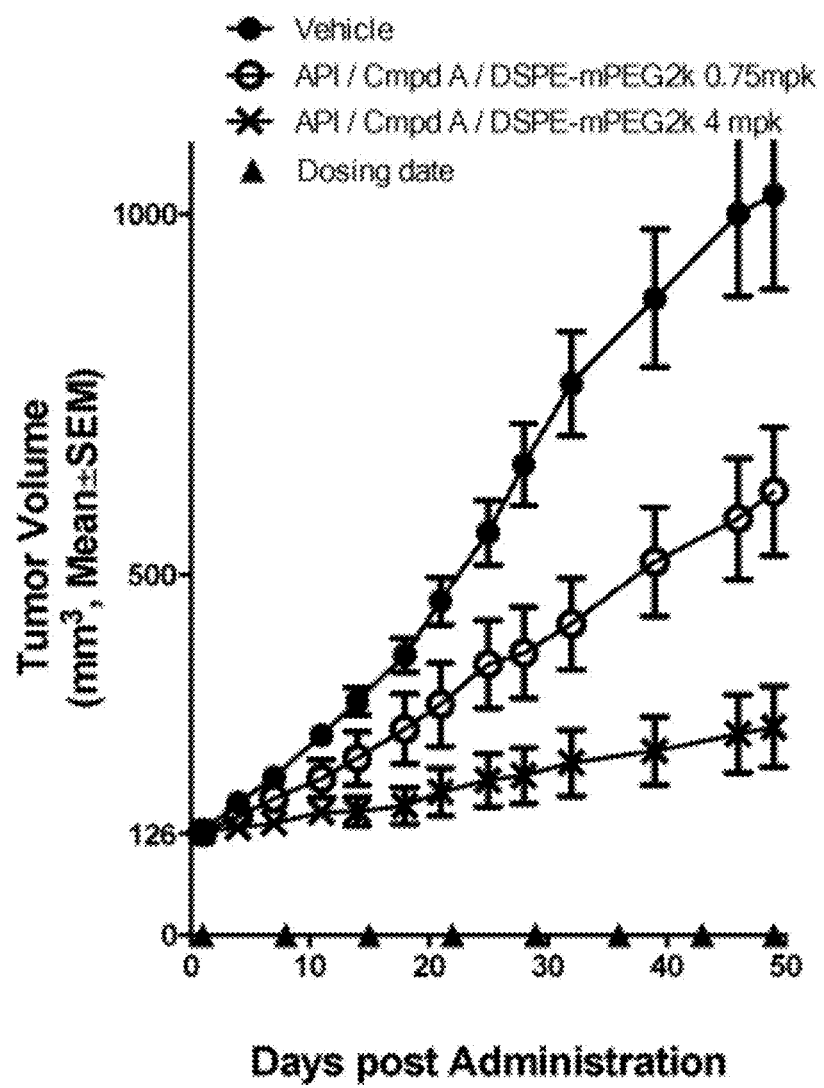
FIG. 2 shows tumor growth inhibition efficacy for a liposomal formulation of GST-π siRNA of this invention in an A549 cell lung cancer sub-Q xenograft model in athymic nude (nu/nu) female mice. The pharmaceutical formulation API(26/52) siRNA GST-π, Compound A 25 mol %, cholesterol 30 mol %, DOPE 20 mol %, DOPC 20 mol %, DSPE-mPEG-2000 5 mol %) showed significant tumor growth inhibition efficacy within a few days after administration. After 49 days, the pharmaceutical formulation with GST-π siRNA showed markedly advantageous tumor growth inhibition efficacy, with tumor volume reduced by greater than 3.4-fold for a 4 mg/kg dose as compared to vehicle control.

FIG. 2 shows tumor growth inhibition efficacy for a liposomal formulation of GST-π siRNA of this invention in an A549 cell lung cancer sub-Q xenograft model in athymic nude (nu/nu) female mice. The pharmaceutical formulation (siRNA GST-π, Compound A 25 mol %, cholesterol 30 mol %, DOPE 20 mol %, DOPC 20 mol %, DSPE-mPEG-2000 5 mol %) showed significant tumor growth inhibition efficacy within a few days after administration. After 49 days, the pharmaceutical formulation with GST-π siRNA showed markedly advantageous tumor growth inhibition efficacy, with tumor volume reduced by greater than 3.4-fold for a 4 mg/kg dose as compared to vehicle control.

Tumor growth inhibition effects of treatment were evaluated and results showed dose-dependent tumor growth inhibition. At 4 mg/kg the T/C Ratio at Day 49 was 30% (tumor growth inhibition ratio, 100% for vehicle control), the percentage of tumor growth inhibition was 70% (TGI %, 0% for vehicle control), and the tumor doubling time was 47 days ($t_D$, 16 days for vehicle control). No significant body weight loss was noticed.

Dose levels at 0.75 and 4 mg/kg of each formulation were administered to animals for eight consecutive weeks following once-a-week (QW×8) dosing regimen. Both efficacy (tumor volume reduction curve, T/C ratio, % TGI and $t_D$) and safety (body weight and overt clinical signs) were monitored in this study. Tissue samples (tumor, lung, and liver) were collected 24 hours post the final dose. There were 7 animals per group (145±5 mm), with a dosing volume at 10 mL/kg. Endpoints were: (1) BW: daily for first week, twice/week for the following three weeks post first dosing, once/week for the rest of week if additional doses were given. (2) Tumor measurement: twice/for first four weeks, once/for the rest of weeks if additional doses were given. On dosing days, frozen formulation vials were removed from −80° C. and −20° C. freezers, respectively.

The pharmaceutical formulation was used from frozen formulation stock, vials stood at room temperature for approximately 30 min. Vials were gently inverted to mix the contents well. The original stock solutions were diluted with appropriate volumes of saline to achieve the corresponding target concentrations prior to IV dosing.

Example protocol for cancer xenograft model. An A549 cell line is obtained from ATCC. The cells are maintained in culture medium supplemented with 10% Fetal Bovine Serum and 100 U/ml penicillin and 100 µg/ml streptomycin. Cells are split 48 hrs before inoculation so that cells are in log phase growth when harvested. Cells are lightly trypsinized with trypsin-EDTA and harvested from tissue culture. The number of viable cells is counted and determined in a hemocytometer in the presence of trypan blue (only viable cells are counted). The cells are resuspended to a concentration of $5 \times 10^7$/ml in media without serum. Then the cell suspension is mixed well with ice thawed BD matrigel at 1:1 ratio for injection.

Mice are Charles River Laboratory Athymic Nude (nu/nu) Female Mice, immuno-compromised, 6-8 weeks old, 7-8 mice per group.

For tumor model preparation, each mouse is inoculated subcutaneously in the right flank with 0.1 ml an inoculum of $2.5 \times 10^6$ of A549 cells using a 25 G needle and syringe, one inoculum per mouse. Mice are not anesthetized for inoculation.

For tumor volume measurements and randomization, tumor size is measured to the nearest 0.1 mm. Tumor volumes are calculated using the formula: Tumor volume=length×width$^2$/2. Once the established tumors reach approximately 120-175 mm$^3$, average tumor volume is about 150 mm$^3$, the mice are assigned into the various vehicle control and treatment groups such that the mean tumor volumes in the treated groups are within 10% of the mean tumor volume in the vehicle control group, ideally, the CV % of tumor volume is less than 25%. On the same day, test articles and control vehicle are administered according to the dosing regimen. Tumor volumes are monitored three times for week 1, twice for the rest of weeks, including the day of study termination.

For dosage administration, on the dosing day, the test articles are taken out from −80° C. freezer and thawed on ice. Before applied to syringes, the bottle containing formulation is inverted by hands for a few times. All test articles are dosed by IV, at 10 ml/kg.

For body weight, mice are weighed to the nearest 0.1 g. Body weights are monitored and recorded daily within 7 days post dosing for first dose. Body weights are monitored and recorded twice for weeks, for the rest of weeks, including the day of study termination.

For tumors collection, on 49 days post first dosing, tumor volume is measured, and tumor is dissected for weight measurement, and stored for PD biomarker study. Tumor weight is recorded.

Example 3

A drug product of an embodiment of this invention having a siRNA targeted to GST-π exhibited profound reduction of tumor volume in vivo. The GST-π siRNA provided gene knockdown potency in vivo when administered in a liposomal formulation to the cancer xenograft tumors.

Figure 3:
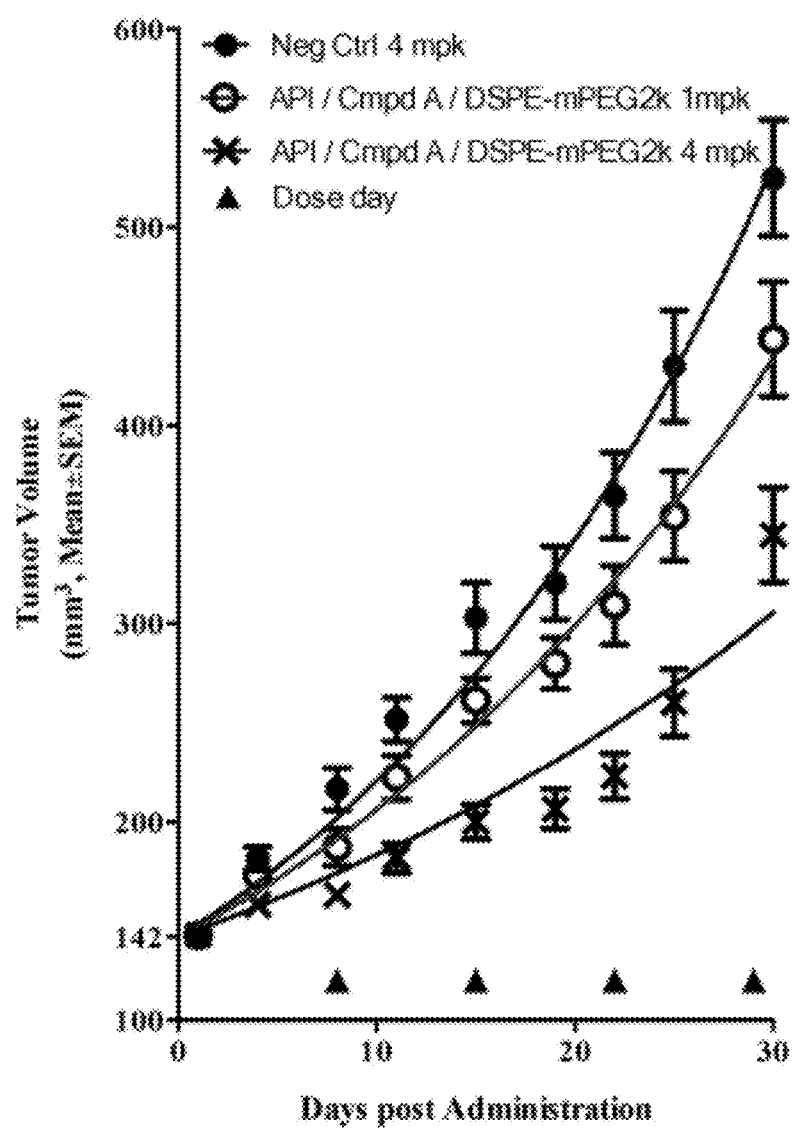
FIG. 3 shows tumor growth inhibition efficacy for a liposomal formulation of GST-π siRNA of this invention in a human H2009 cell lung cancer sub-Q xenograft model in athymic Balb/c nude (nu/nu) female mice. H2009 are lymph node metastasis lung adenocarcinoma cells. The drug solution administered was reconstituted from a lyophilized pharmaceutical solution containing 10 mg/vial of API(26/52) GST-π siRNA. The pharmaceutical solution contained a suspension of the pharmaceutical formulation based on pharmaceutical formulation (siRNA GST-π, Compound A 25 mol %, cholesterol 30 mol %, DOPE 20 mol %, DOPC 20 mol %, DSPE-mPEG-2000 5 mol %), along with lyoprotectants sucrose and 2-hydroxypropyl-β-cyclodextrin, and 27 mg of ascorbic acid and 27 mg of sodium acetate as a buffer. The drug product was reconstituted into a drug solution with 5.6 mL of sterile WFI to yield a reconstituted suspension at 1.5 mg/mL of the API(26/52) GST-π siRNA. The results showed dose-dependent tumor growth inhibition effects of the drug solution in a KRAS mutant subcutaneous (sub-Q) xenograft H2009 NSCLC tumor model.

FIG. 3 shows tumor growth inhibition efficacy for a liposomal formulation of GST-π siRNA of an embodiment of this invention in a human H2009 cell lung cancer sub-Q xenograft model in athymic Balb/c nude (nu/nu) female mice. H2009 are lymph node metastasis lung adenocarcinoma cells. The drug solution administered was reconstituted from a lyophilized pharmaceutical solution containing 10 mg/vial of GST-π siRNA. The pharmaceutical solution contained a suspension of the pharmaceutical formulation based on pharmaceutical formulation (siRNA GST-π, Compound A 25 mol %, cholesterol 30 mol %, DOPE 20 mol %, DOPC 20 mol %, DSPE-mPEG-2000 5 mol %), along with lyoprotectants sucrose and 2-hydroxypropyl-β-cyclodextrin, and 27 mg of ascorbic acid and 27 mg of sodium acetate as a buffer. The drug product was reconstituted into a drug solution with 5.6 mL of sterile WFI to yield a reconstituted suspension at 1.5 mg/mL of the API(26/52) GST-π siRNA. The results showed dose-dependent tumor growth inhibition effects of the drug solution in a KRAS mutant subcutaneous (sub-Q) xenograft H2009 NSCLC tumor model.

The Z-average (Z-ave) particle size for the drug solution was 54 nm (44 nm for negative control), with a particle size distribution PDI of 0.15 (0.09 for negative control).

On dosing days, lyophilized formulation vials were removed from the 20° C. freezer. To prepare 2 mg/mL concentration working solution, 1.2 mL of water for injection (WFI) were added to reconstitute the lyophile cake. Vials were left at room temperature for 5 minutes, gently swirled for 2 minutes and then left at room temperature for additional 20 minutes. A final dilution round was made by adding 5.4 mL of saline to 0.6 mL of 2 mg/mL solution to obtain 0.2 mg/mL dosing solution.

Mice were administered the negative control at a dosage of 4 mpk and test drug at doses of 1 and 4 mpk with dosing volumes of 10 mL/kg. The dosing regimen was once-a-week (QW) for four consecutive weeks.

The drug solution reconstituted from lyophilized pharmaceutical formulation (siRNA GST-π, Compound A 25 mol %, cholesterol 30 mol %, DOPE 20 mol %, DOPC 20 mol %, DSPE-mPEG-2000 5 mol %) showed significant tumor growth inhibition efficacy within a few days after administration. After 29 days, the pharmaceutical formulation with GST-π siRNA showed markedly advantageous tumor growth inhibition efficacy, with tumor volume reduced by greater than 1.5-fold for a 4 mg/kg dose as compared to negative control.

In conclusion, the drug solution demonstrated tumor growth inhibition efficacy against human KRAS mutant H2009 sub-Q xenograft tumors. Anti-tumor activity was shown to be dose-dependent.

TABLE 3

Tumor growth inhibition assessment

| Treatment (analysis day 30) | Dose Level (mpk), QWx5 | T/C Ratio (%) | TGI (%) | $t_D$ (Day) |
|---|---|---|---|---|
| Vehicle (Saline) | 0 | 100 | 0 | 13 |
| Negative Control | 4.0 | 78 | 22 | 16 |
| Drug soln constituted | 1.0 | 66 | 34 | 17 |
| Drug soln constituted | 4.0 | 51 | 49 | 27 |

Tumor growth inhibition effects of treatment were evaluated and results showed dose-dependent tumor growth inhibition. At 4 mg/kg the T/C Ratio at Day 29 was 51% (tumor growth inhibition ratio, 78% for negative control), the percentage of tumor growth inhibition was 49% (TGI %, 22% for negative control), and the tumor doubling time was 27 days ($t_D$, 16 days for negative control). Study animals exhibited slight body weight loss (less than 10%) during the first week following treatments but then returned to base level followed by body weight increase thereafter. No overt clinical signs were observed for the other remaining animals throughout the entire study.

Protocol: Human H2009 cell line was obtained from ATCC (from ATCC® CCL-5911 ™, Manassas, Va.). Cells were maintained in DMEM/F12 (Cat #30-2006) culture medium supplemented with 5% Fetal Bovine Serum (Lot # AAM211829 from HyClone/VWR), 100 U/ml penicillin (Lot #1780186 from Gibco) and 100 μg/ml streptomycin (Lot #1780186 from Gibco); additional ingredients were added for with final formulation as follows: 0.005 mg/ml Insulin, 0.01 mg/ml Transferrin, 30 nM sodium selenite, 10 nM hydrocortisone, 4.5 mM L-glutamine and maintained in a humidified atmosphere with 5% $CO_2$ for 48 hrs. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were then resuspended to a concentration of $3\times10^7$/ml in media without serum. The cell suspension was mixed well with ice thawed BD Matrigel (Lot #7058007 from VWR) at 1:1 ratio for injection to establish the xenograft tumor in the mice.

Athymic Balb/c nude (nu/nu) female mice at 6-8 weeks were purchased from Charles River Laboratories and housed at animal facility. Each mouse was inoculated subcutaneously in the right flank with 0.1 mL inoculum of $1.5\times10^6$ of NCI H2009 cells using 25 G1/2 needle and 1 ml syringe (one inoculums per mouse). Tumor size was measured to the nearest 0.1 mm. Tumor volumes were calculated using the formula: Tumor volume=(length×width$^2$)/2. Once the established tumors reached approximately 120-170 mm$^3$ (average tumor volume at 145 mm$^3$), the mice were randomized into the vehicle control and three treatment groups. Randomization was performed mainly based on two criteria: 1) mean tumor volume in each treatment group was within 10% of corresponding value of the vehicle control group, and 2) CV % of tumor volume within each group was less than 15%. On the same day, test articles and control vehicle were administered according to dosing regimen. Tumor volumes were monitored three times for week 1, twice for the rest of weeks, including study termination day. Body weight was also checked across all study groups to ensure no extremes were included in any study groups. For this study, seven mice per group were used.

Body weight was measured daily for the first week and twice a week for the remaining study period. Tumor size was measured twice a week for the study period. Animals on study were observed daily for overt clinical signs.

Example 4

A pharmaceutical formulation of an embodiment of this invention having a siRNA targeted to GST-π exhibited profound reduction of cancer xenograft tumors in vivo. The GST-π siRNA provided gene knockdown potency in vivo when administered in a liposomal formulation to the cancer xenograft tumors.

Figure 4:
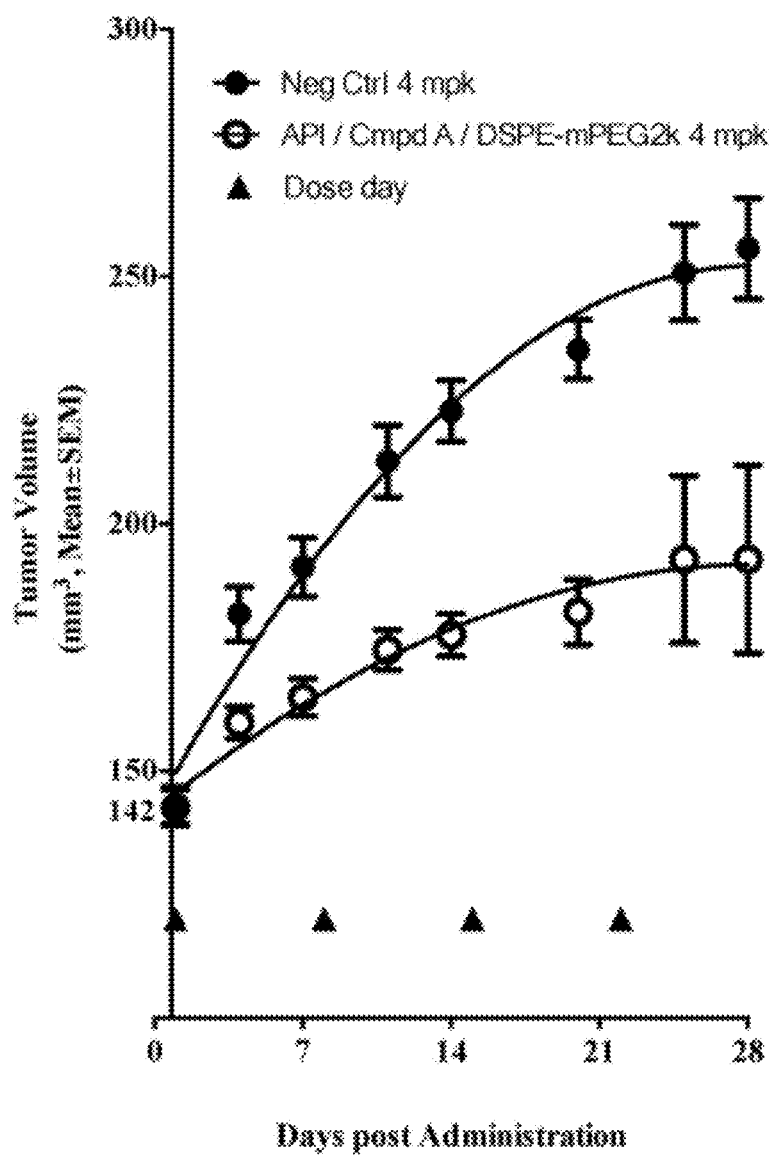
FIG. 4 shows tumor growth inhibition efficacy for a liposomal formulation of GST-π siRNA of this invention in a human H23 cell lung cancer sub-Q xenograft model in athymic Balb/c nude (nu/nu) female mice. H23 are adenocarcinoma; non-small cell lung cancer. The administered composition contained a suspension of the pharmaceutical formulation based on pharmaceutical formulation API(26/52) siRNA GST-π, Compound A 25 mol %, cholesterol 30 mol %, DOPE 20 mol %, DOPC 20 mol %, DSPE-mPEG-2000 5 mol %), and 27 mg of ascorbic acid and 27 mg of sodium acetate as a buffer. The results showed dose-dependent tumor growth inhibition effects of the drug solution in a KRAS mutant subcutaneous (sub-Q) xenograft H23 NSCLC tumor model.

FIG. 4 shows tumor growth inhibition efficacy for a liposomal formulation of GST-π siRNA of an embodiment of this invention in a human H23 cell lung cancer sub-Q xenograft model in athymic Balb/c nude (nu/nu) female mice. H23 are adenocarcinoma; non-small cell lung cancer. The administered composition contained a suspension of the pharmaceutical formulation based on pharmaceutical formulation (siRNA GST-π, Compound A 25 mol %, cholesterol 30 mol %, DOPE 20 mol %, DOPC 20 mol %, DSPE-mPEG-2000 5 mol %), and 27 mg of ascorbic acid and 27 mg of sodium acetate as a buffer. The results showed dose-dependent tumor growth inhibition effects of the drug solution in a KRAS mutant subcutaneous (sub-Q) xenograft H23 NSCLC tumor model.

The Z-ave particle size for the pharmaceutical composition was 47 nm (44 nm for negative control), with a particle size distribution PDI of 0.07 (0.09 for negative control).

On dosing days, frozen formulation vials were removed from −80° C. freezer and thawed at room temperature for approximately 30 minutes. Vials were gently inverted to mix the contents. The original stock solutions were diluted with an appropriate volume of saline to achieve the target concentrations prior to IV dosing.

Mice were administered the negative control at a dosage of 4 mpk and test drug at a dosage of 4 mpk with dosing volumes of 10 mL/kg. The dosing regimen was once-a-week (QW) for four consecutive weeks.

The pharmaceutical composition (siRNA GST-π, Compound A 25 mol %, cholesterol 30 mol %, DOPE 20 mol %, DOPC 20 mol %, DSPE-mPEG-2000 5 mol %) showed significant tumor growth inhibition efficacy within a few days after administration. After 28 days, the pharmaceutical formulation with GST-π siRNA showed markedly advantageous tumor growth inhibition efficacy, with tumor volume reduced by greater than 1.3-fold for a 4 mg/kg dose as compared to negative control.

In conclusion, the drug solution demonstrated tumor growth inhibition efficacy against human KRAS mutant H23 sub-Q xenograft tumors. Anti-tumor activity was shown to be dose-dependent.

TABLE 4

Tumor growth inhibition assessment Day 28

| Treatment (analysis day 28) | Dose Level (mpk), QWx4 | T/C Ratio (%) | TGI (%) |
| --- | --- | --- | --- |
| Vehicle | 0 | 100 | 0 |
| Negative Control | 4.0 | 69 | 31 |
| Formulation | 4.0 | 52 | 48 |

Tumor growth inhibition effects of treatment were evaluated and results showed dose-dependent tumor growth inhibition. At 4 mg/kg the T/C Ratio at Day 28 was 52% (tumor growth inhibition ratio, 69% for negative control), the percentage of tumor growth inhibition was 48% (TGI %, 31% for negative control).

Figure 5:
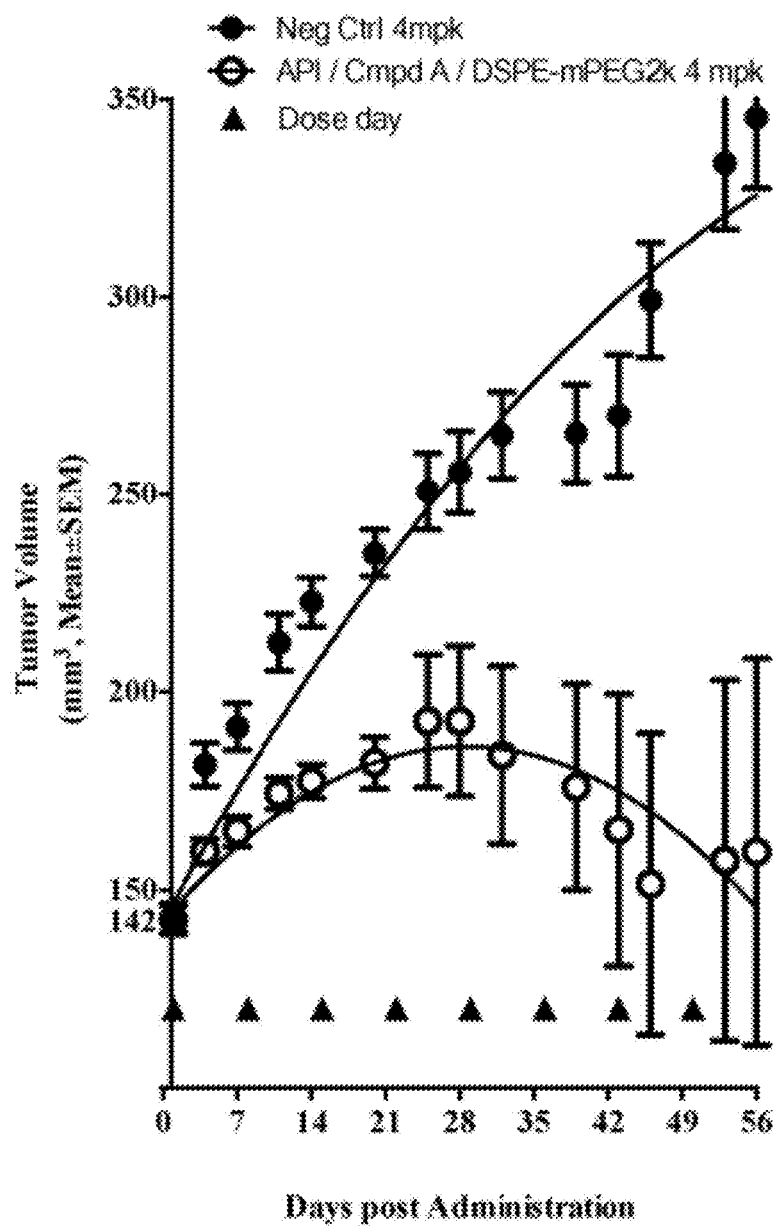
FIG. 5 shows tumor growth inhibition efficacy for a liposomal formulation of GST-π siRNA of this invention in a human H23 cell lung cancer sub-Q xenograft model in athymic Balb/c nude (nu/nu) female mice. The administered composition contained a suspension of the pharmaceutical formulation based on pharmaceutical formulation API(26/52) siRNA GST-π, Compound A 25 mol %, cholesterol 30 mol %, DOPE 20 mol %, DOPC 20 mol %, DSPE-mPEG-2000 5 mol %), and 27 mg of ascorbic acid and 27 mg of sodium acetate as a buffer. The results at day 56 showed dose-dependent tumor growth inhibition effects of the drug solution in a KRAS mutant subcutaneous (sub-Q) xenograft H23 NSCLC tumor model.

FIG. 5 shows tumor growth inhibition efficacy for a liposomal formulation of GST-π siRNA of this invention in a human H23 cell lung cancer sub-Q xenograft model in athymic Balb/c nude (nu/nu) female mice. The administered composition contained a suspension of the pharmaceutical formulation based on pharmaceutical formulation (siRNA GST-π, Compound A 25 mol %, cholesterol 30 mol %, DOPE 20 mol %, DOPC 20 mol %, DSPE-mPEG-2000 5 mol %), and 27 mg of ascorbic acid and 27 mg of sodium acetate as a buffer. The results showed dose-dependent tumor growth inhibition effects of the drug solution in a KRAS mutant subcutaneous (sub-Q) xenograft H23 NSCLC tumor model.

The pharmaceutical composition (siRNA GST-π, Compound A 25 mol %, cholesterol 30 mol %, DOPE 20 mol %, DOPC 20 mol %, DSPE-mPEG-2000 5 mol %) showed significant tumor growth inhibition efficacy within a few days after administration. After 56 days, the pharmaceutical formulation with GST-π siRNA showed markedly advantageous tumor growth inhibition efficacy, with tumor volume reduced by greater than 2-fold for a 4 mg/kg dose as compared to negative control.

TABLE 5

Tumor growth inhibition assessment Day 56

| Treatment (analysis day 56) | Dose Level (mpk), QWx8 | T/C Ratio (%) | TGI (%) |
|---|---|---|---|
| Vehicle | 0 | 100 | 0 |
| Negative Control | 4.0 | 63 | 37 |
| Formulation | 4.0 | 29 | 71 |

Protocol: Human NCI-H23 cell line was obtained from ATCC (C/N: CRL-5800, L/N: 63990092, Manassas, Va.). Cells were maintained in RPMI-1640 media (Lot # AAF202601 from HyClone/VWR) containing 10% Fetal Bovine Serum (Lot # AAM211829 from HyClone/VWR), 100 U/mL penicillin (Lot #1780186 from Gibco) and 100 µg/mL streptomycin (Lot #1780186 from Gibco) in a humidified atmosphere with 5% $CO_2$ for 48 hrs. Cultured cells were passaged three times and then harvested prior to animal inoculation. Harvested cells were then re-suspended to a concentration of $3 \times 10^7$ cells/mL in serum free RPMI media. The cell suspension was mixed well with ice thawed BD Matrigel (Lot #7058007 from VWR) at 1:1 ratio for the injection to establish the xenograft tumor in the mice.

Athymic Balb/c nude (nu/nu) female mice at 6-8 weeks were purchased from Charles River Laboratories and housed at animal facility. Each mouse was inoculated subcutaneously in the right flank with 0.1 mL inoculum of $1.5 \times 10^6$ cells. Tumor size was measured to the nearest 0.1 mm. Tumor volumes were calculated using the formula: Tumor volume=(length×width$^2$)/2. Once the established tumors reached approximately 120-170 mm$^3$ (average tumor volume at 145 mm$^3$), the mice were randomized into the vehicle control and two treatment groups. Randomization was performed mainly based on two criteria: 1) mean tumor volume in each treatment group was within 10% of corresponding value of the vehicle control group, and 2) CV % of tumor volume within each group was less than 15%. Body weight was also checked across all study groups to ensure no extremes were included in any study groups. For this study, seven mice per group were used.

Example 5

Lipid nanoparticle formulations provide surprisingly high delivery to lung.

Figure 6:
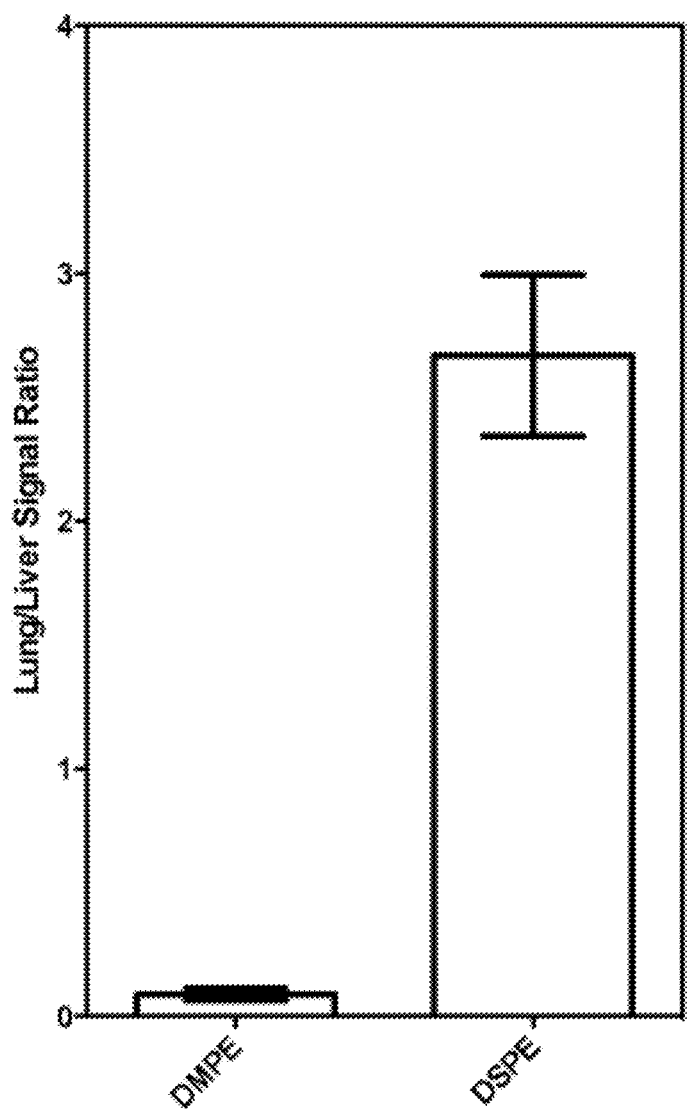
FIG. 6 shows the ratio of distribution of lung to liver in vivo mouse for formulations of this invention. The administered composition was based on pharmaceutical two formulations, "DMPE (left):" (API siRNA, Compound A 25 mol %, cholesterol 30 mol %, DOPE 20 mol %, DOPC 20 mol %, DMPE-mPEG-2000 5 mol %), and "DSPE (right):" (API siRNA, Compound A 25 mol %, cholesterol 30 mol %, DOPE 20 mol %, DOPC 20 mol %, DSPE-mPEG-2000 5 mol %). The results showed that the ratio of the distribution of active agent to lung over liver in vivo mouse was 30-fold higher for a formulation based on DSPE-mPEG-2000, as compared to DMPE-mPEG-2000.

FIG. 6 shows the ratio of distribution of lung to liver in vivo mouse for embodiments of formulations of this invention. The administered composition was based on two pharmaceutical formulations, "DMPE (left):" (API siRNA, Compound A 25 mol %, cholesterol 30 mol %, DOPE 20 mol %, DOPC 20 mol %, DMPE-mPEG-2000 5 mol %), and "DSPE (right):" (API siRNA, Compound A 25 mol %, cholesterol 30 mol %, DOPE 20 mol %, DOPC 20 mol %, DSPE-mPEG-2000 5 mol %). The results showed that the ratio of the distribution of active agent to lung over liver in vivo mouse was surprisingly about 30-fold higher for a formulation based on DSPE-mPEG-2000, as compared to DMPE-mPEG-2000.

Example 6

Lipid nanoparticle formulations comprising Compound A and DSPE-PEG2k provide surprisingly high delivery to lung.

Figure 7:
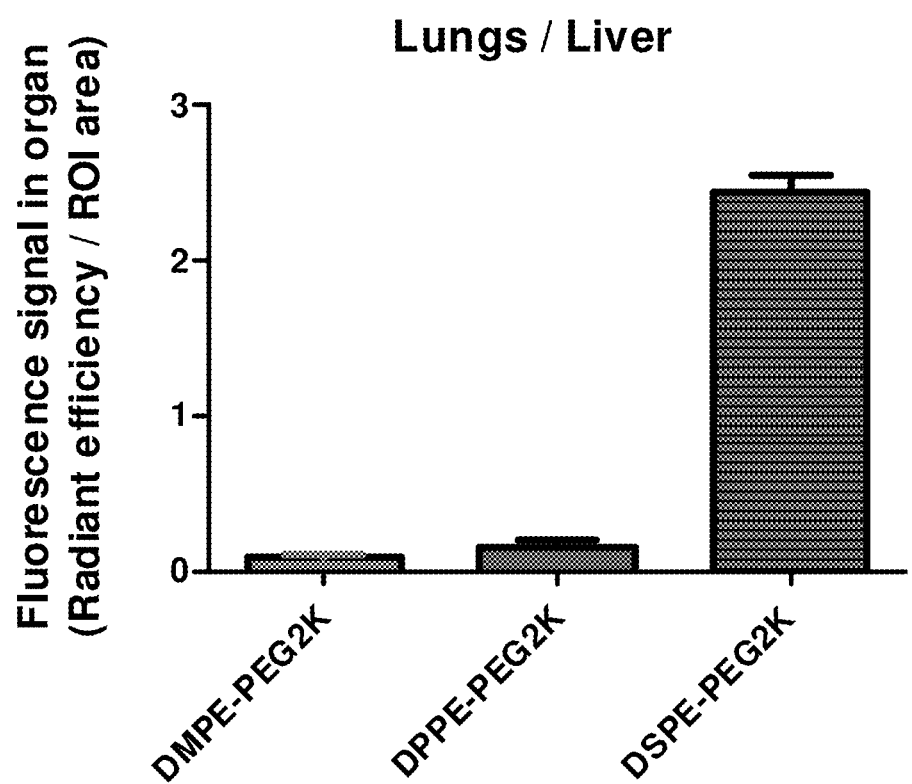
FIG. 7 shows the ratio of distribution of lung to liver in vivo mouse for embodiments of formulations of this invention containing a liposome encapsulated API siRNA.

FIG. 7 shows the ratio of distribution of lung to liver in vivo mouse for embodiments of formulations of this invention containing a lipid encapsulated API siRNA. The administered compositions were based on three pharmaceutical formulations as described in the table below. The results showed that the ratio of the distribution of siRNA active agent to lung over liver in vivo mouse was surprisingly 25-fold to 30-fold higher for a formulation based on DSPE-mPEG-2000, as compared to otherwise identical formulations based DMPE-mPEG-2000 or DPPE-mPEG-2000.

| Lipid Formulation | Lipid Molar Ratio |
|---|---|
| Compound A:Cholesterol:DOPE:DOPC:DMPE-PEG2k | 25:30:20:20:5 |
| Compound A:Cholesterol:DOPE:DOPC:DPPE-PEG2k | 25:30:20:20:5 |
| Compound A:Cholesterol:DOPE:DOPC:DSPE-PEG2k | 25:30:20:20:5 |

Example 7

Lipid nanoparticle formulations comprising a lipid (Compound A, Compound B or Compound C) and DSPE-PEG2k provide surprisingly high delivery to lung.

Figure 8:
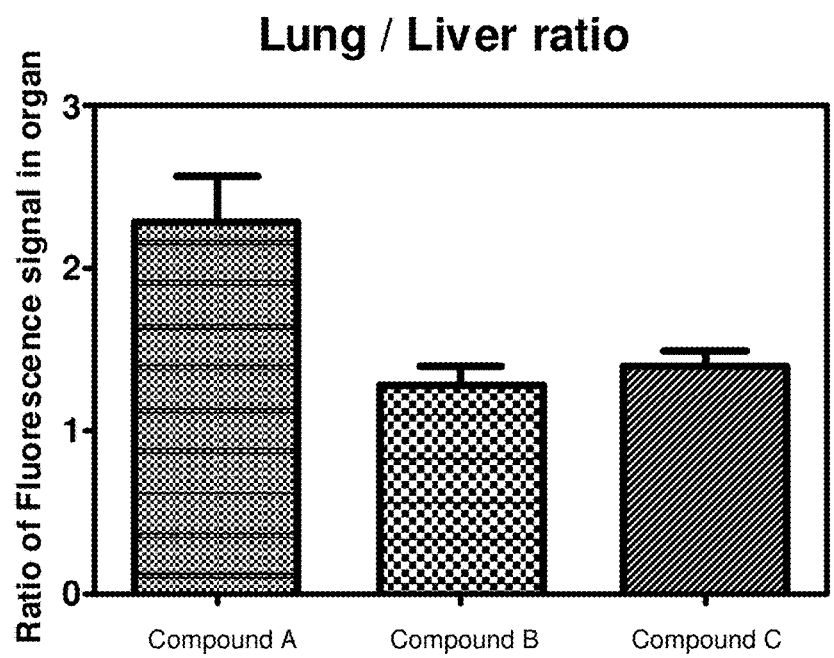
FIG. 8 shows the ratio of distribution of lung to liver in vivo mouse for embodiments of formulations of this invention containing a liposome encapsulated API siRNA.
Figure 8:
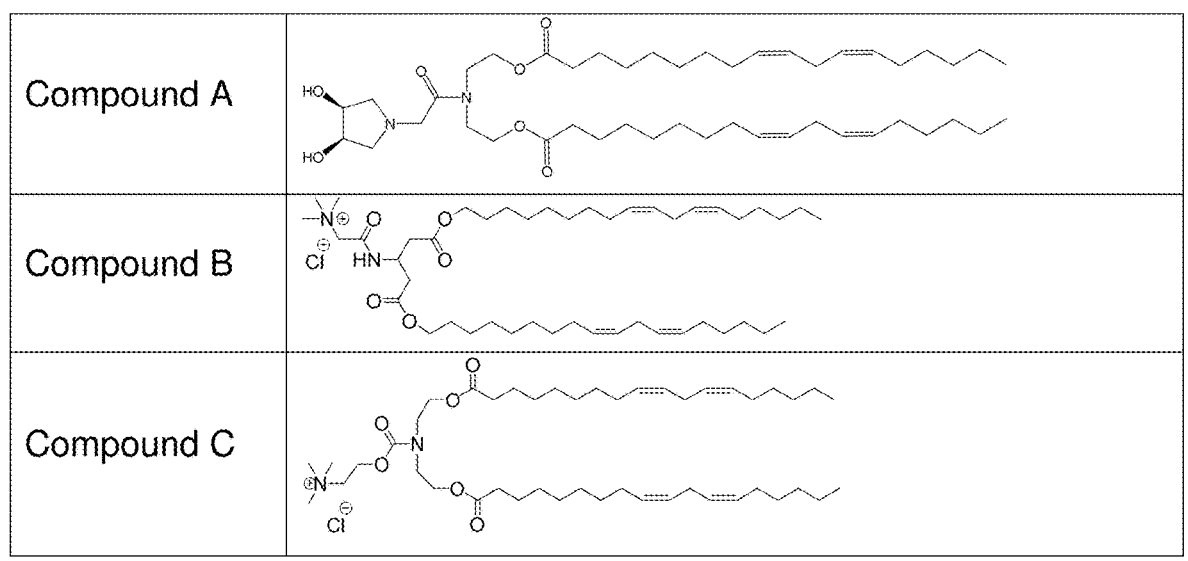

FIG. 8 shows the ratio of distribution of lung to liver in vivo mouse for embodiments of formulations of this invention containing a lipid encapsulated API siRNA. The administered compositions were based on three pharmaceutical formulations utilizing different lipids (Compound A, Compound B and Compound C) as detailed in the table below.

| Lipid Formulation | Lipid Molar Ratio |
|---|---|
| Compound A:Cholesterol:DOPE:DOPC:DSPE-PEG2k | 25:30:20:20:5 |
| Compound B:Cholesterol:DOPE:DOPC:DSPE-PEG2k | 25:30:20:20:5 |
| Compound C:Cholesterol:DOPE:DOPC:DSPE-PEG2k | 25:30:20:20:5 |

The results showed that the ratio of the distribution of siRNA active agent to lung over liver in vivo mouse was greater than 1.0 for all three lipids, and surprisingly much higher for a formulation based on Compound A, as compared to otherwise identical formulations based on lipids Compound B and Compound C having the chemical structures illustrated in FIG. 8.

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A pharmaceutical composition comprising
   (a) a nucleic acid active pharmaceutical ingredient (nucleic acid API);
   (b) a compound having the following Formula II:

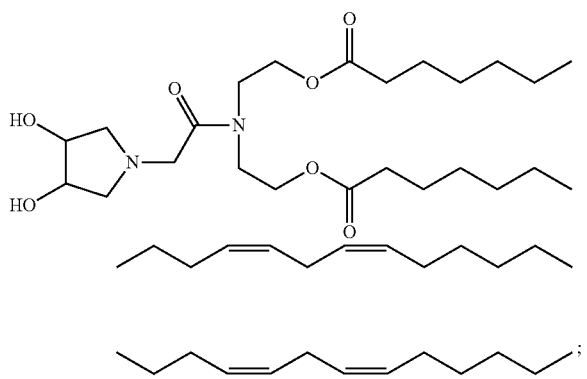

(c) a DSPE lipid comprising a polyethyleneglycol (PEG) region, a multi-branched PEG region, a methoxypolyethyleneglycol (mPEG) region, a carbonyl-methoxypolyethyleneglycol region, or a polyglycerine region;
   (d) a sterol lipid; and
   (e) one or more neutral lipids other than the DSPE lipid and the sterol lipid;
   wherein the DSPE lipid is from 4 mol % to 6 mol % of the total lipids of the composition.

2. The pharmaceutical composition of claim 1, wherein the compound of Formula II is from 15 mol % to 35 mol % of the total lipids of the composition.

3. The pharmaceutical composition of claim 1, wherein the sterol lipid is from 25 mol % to 40 mol % of the total lipids of the composition.

4. The pharmaceutical composition of claim 1, wherein the sterol lipid is cholesterol.

5. The pharmaceutical composition of claim 1, wherein the DSPE lipid comprises a methoxypolyethyleneglycol (mPEG) region.

6. The pharmaceutical composition of claim 5, wherein the DSPE lipid is DSPE-mPEG-2000.

7. The pharmaceutical composition of claim 1, wherein the one or more neutral lipids other than the DSPE lipid and the sterol lipid are 1,2-dioleoyl-sn-Glycero-3-Phosphocholine (DOPC) and 1,2-dioleoyl-sn-glycero-3-phosphoethanolamine (DOPE).

8. The pharmaceutical composition of claim 7, wherein the sum of DOPC and DOPE is from 25 mol % to 45 mol % of the total lipids of the composition, and wherein each of DOPC and DOPE is present at 5 mol % to 40% mol %.

9. The pharmaceutical composition of claim 7, wherein the sterol lipid is cholesterol, and wherein the cholesterol, DOPC, and DOPE combined comprise 50 mol % to 85 mol % of the total lipids of the composition.

10. The pharmaceutical composition of claim 7, wherein
    the sterol lipid is cholesterol;
    the DSPE lipid is DSPE-mPEG-2000;
    the compound of Formula II comprises 15 mol % to 35 mol % of the total lipids of the composition;
    cholesterol, DOPC, and DOPE combined comprise 50 mol % to 85 mol % of the total lipids of the composition; and
    DSPE-mPEG-2000 comprises from 4 mol % to 6 mol % of the total lipids of the composition;
    with the condition that the compound of Formula II, cholesterol, DOPC, DOPE, and DSPE-mPEG-2000 combined comprise at least 97 mol % of the total lipids of the composition.

11. The pharmaceutical composition of claim 10, wherein the compound of Formula II, cholesterol, DOPC, DOPE, and DSPE-mPEG-2000 combined comprise 100 mol % of the total lipids of the composition.

12. The pharmaceutical composition of claim 7, wherein
    the sterol lipid is cholesterol;
    the DSPE lipid is DSPE-mPEG-2000;
    the compound of Formula II comprises 20 mol % to 30 mol % of the total lipids of the composition;
    cholesterol comprises 25 mol % to 35 mol % of the total lipids of the composition;
    DOPC and DOPE combined comprise 30 mol % to 50 mol % of the total lipids of the composition; and
    DSPE-mPEG-2000 comprises from 4 mol % to 6 mol % of the total lipids of the composition;
    with the condition that the compound of Formula II, cholesterol, DOPC, DOPE, and DSPE-mPEG-2000 combined comprise at least 97 mol % of the total lipids of the composition.

13. The pharmaceutical composition of claim 12, wherein the compound of Formula II, cholesterol, DOPC, DOPE, and DSPE-mPEG-2000 combined comprise 100 mol % of the total lipids of the composition.

14. A pharmaceutical composition comprising:
(a) a nucleic acid active pharmaceutical ingredient (nucleic acid API);
(b) a compound having the following Formula II:

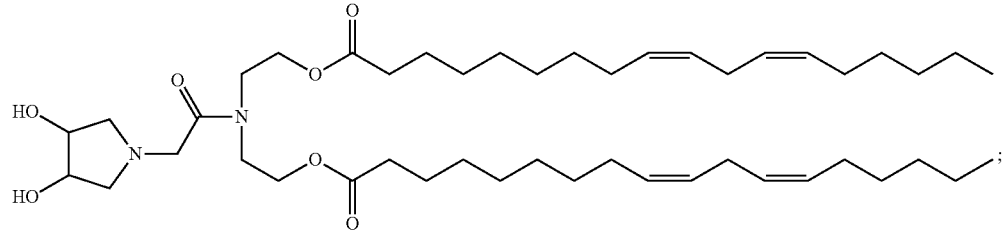 [SMILES: CCCCC/C=C\C/C=C\CCCCCCCC(=O)OCCN(CCOC(=O)CCCCCCC/C=C\C/C=C\CCCCC)C(=O)CN1CC(O)C(O)C1]

(c) a DSPE lipid comprising a polyethyleneglycol (PEG) region, a multi-branched PEG region, a methoxypolyethyleneglycol (mPEG) region, a carbonyl-methoxypolyethyleneglycol region, or a polyglycerine region;
(d) a sterol lipid; and
(e) one or more neutral lipids other than the DSPE lipid and the sterol lipid;
wherein the DSPE lipid is from 4 mol % to 6 mol % of the total lipids of the composition;
wherein the nucleic acid API is API(26/52), an siRNA targeted to GST-π having:
the sense strand sequence GAAGCCUUUUGAGACCC UAUU (SEQ ID NO: 26); and
the antisense strand sequence fUAGgGuCuCAAAAGGC UUCUU (SEQ ID NO.52);
wherein A, G, C and U refer to ribo-A, ribo-G, ribo-C and ribo-U, respectively; lower case letters a, u, g, c, t, when present, refer to 2'-deoxy-A, 2'-deoxy-U, 2'-deoxy-G, 2'-deoxy-C, and 2'-deoxy-T respectively; underlining refers to 2'-OMe substitution; and the lower case letter f refers to 2'-deoxy-2'-fluoro substitution.

15. The pharmaceutical composition of claim 14, wherein the compound having the Formula II is Compound A having the formula:

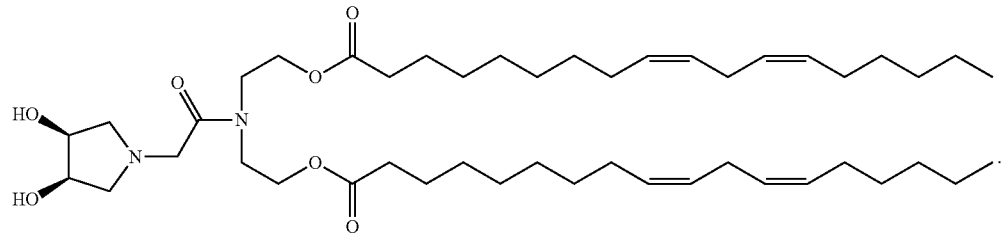 [SMILES: CCCCC/C=C\C/C=C\CCCCCCCC(=O)OCCN(CCOC(=O)CCCCCCC/C=C\C/C=C\CCCCC)C(=O)CN1C[C@@H](O)[C@@H](O)C1]

16. The pharmaceutical composition of claim 1, wherein the nucleic acid API is a siRNA targeted to GST-π comprising a sense strand and an antisense strand, wherein the sense strand is set forth by SEQ ID NO: 1 (GAAGCCUUUUGAGACCCUANN) and the antisense strand is set forth by SEQ ID NO: 27 (UAGGGUCUCAAAAGGCUUCNN), wherein N is selected from the group of A, C, G, U, 2'-OMe-U, a, c, g, u, t, an inverted nucleotide, and a chemically modified nucleotide, and wherein A, G, C and U refer to ribo-A, ribo-G, ribo-C and ribo-U, respectively; and lower case letters a, u, g, c, t, when present, refer to 2'-deoxy-A, 2'-deoxy-U, 2'-deoxy-G, 2'-deoxy-C, and 2'-deoxy-T, respectively.

17. The pharmaceutical composition of claim 15, comprising
  (a) API(26/52),
  (b) Compound A (24.985 mol % of total lipids),
  (c) DSPE-mPEG-2000 (4.992 mol % of total lipids),
  (d) semi-synthetic cholesterol (30.015 mol % of total lipids), and
  (e) DOPE (19.989 mol % of total lipids), and DOPC (20.019 mol % of total lipids).

* * * * *